United States Patent
Park et al.

(10) Patent No.: US 6,928,324 B2
(45) Date of Patent: Aug. 9, 2005

(54) STIMULATION DEVICE FOR SLEEP APNEA PREVENTION, DETECTION AND TREATMENT

(75) Inventors: Euljoon Park, Stevenson Ranch, CA (US); Steve Koh, Rowland Heights, CA (US); Gene A. Bornzin, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 539 days.

(21) Appl. No.: 10/077,048

(22) Filed: Feb. 14, 2002

(65) Prior Publication Data
US 2003/0153953 A1 Aug. 14, 2003

(51) Int. Cl.⁷ ............................................. A61N 1/365
(52) U.S. Cl. .............................. 607/20; 607/18; 607/42
(58) Field of Search ........................ 607/42, 9, 17–28

(56) References Cited

U.S. PATENT DOCUMENTS

| | | | |
|---|---|---|---|
| 4,644,954 A | 2/1987 | Wittkampf et al. ... | 128/419 PG |
| 4,759,366 A | 7/1988 | Callaghan ............ | 128/419 PG |
| 4,815,469 A | 3/1989 | Cohen et al. ............ | 128/634 |
| 5,040,538 A | 8/1991 | Mortazavi .............. | 128/633 |
| 5,113,869 A | 5/1992 | Nappholz et al. ........ | 128/634 |
| 5,161,527 A | 11/1992 | Nappholz et al. ...... | 128/419 PG |
| 5,184,615 A | 2/1993 | Nappholz et al. ...... | 128/419 PG |
| 5,188,106 A | 2/1993 | Nappholz et al. ...... | 128/419 PG |
| 5,466,254 A | 11/1995 | Helland ................. | 607/123 |
| 5,476,483 A | 12/1995 | Bornzin et al. .......... | 607/17 |
| 5,485,851 A | 1/1996 | Erickson ................. | 128/716 |
| 5,549,650 A | 8/1996 | Bornzin et al. .......... | 607/17 |
| 5,614,246 A | 3/1997 | Mund et al. ............. | 427/2.24 |
| 5,626,622 A | 5/1997 | Cooper .................. | 607/18 |
| 5,643,327 A | 7/1997 | Dawson et al. .......... | 607/24 |
| 5,778,223 A | 7/1998 | Velissaropoulos et al. .. | 395/611 |
| 5,800,467 A | 9/1998 | Park et al. .............. | 607/17 |
| 5,819,062 A | 10/1998 | Srikantappa ............. | 395/500 |
| 5,970,494 A | 10/1999 | Velissaropoulos et al. .. | 707/102 |
| 5,974,340 A | 10/1999 | Kadhiresan ............. | 607/18 |
| 5,991,661 A | 11/1999 | Park et al. .............. | 607/19 |
| 6,029,088 A | 2/2000 | Budgifvars et al. ....... | 607/27 |
| 6,052,622 A | 4/2000 | Holmström ............. | 607/28 |
| 6,058,328 A | 5/2000 | Levine et al. ............ | 607/14 |
| 6,064,910 A | 5/2000 | Andersson et al. ....... | 607/20 |
| 6,126,611 A * | 10/2000 | Bourgeois et al. ........ | 600/529 |
| 6,128,534 A | 10/2000 | Park et al. .............. | 607/17 |
| 6,132,384 A | 10/2000 | Christopherson et al. ... | 600/529 |
| 6,259,948 B1 | 7/2001 | Florio et al. ............ | 607/9 |
| 6,266,564 B1 | 7/2001 | Hill et al. ............... | 607/9 |
| 6,272,381 B1 | 8/2001 | Callaghan et al. ........ | 607/26 |
| 6,480,733 B1 | 11/2002 | Turcott ................. | 600/516 |
| 6,574,507 B1 * | 6/2003 | Bonnet .................. | 607/20 |
| 6,641,542 B2 * | 11/2003 | Cho et al. ............... | 600/529 |
| 2002/0193697 A1 | 12/2002 | Cho et al. ............... | 600/529 |

FOREIGN PATENT DOCUMENTS

| | | | |
|---|---|---|---|
| EP | 0 940 155 A2 | 2/1999 | ............ A61N/1/36 |
| EP | 1 151 718 A2 | 4/2001 | ......... A61B/5/0205 |
| WO | WO 00/01438 | 1/2000 | .......... A61M/16/00 |

OTHER PUBLICATIONS

Millar, et al., "The Entrainment of Low Frequency Breathing Periodicity", CHEST/98/5, pp:1143–1148 (Nov. 1990).

(Continued)

*Primary Examiner*—George R. Evanisko

(57) ABSTRACT

An implantable cardiac stimulation device comprises a metabolic demand sensor, an activity sensor, and one or more pulse generators. The metabolic demand sensor and activity sensor can sense metabolic demand and physical activity parameters, respectively. The pulse generators can generate cardiac pacing pulses with timing based on a comparison of the metabolic demand and physical activity parameters. The timed cardiac pacing pulses can prevent a sleep apnea condition.

22 Claims, 11 Drawing Sheets

OTHER PUBLICATIONS

Hanly, et al., "Respiraiton and Abnormal Sleep in Patients with Congestive Heart Failure", CHEST/96/3, pp: 480–488 (Sep. 1989).

Saul, et al., "Nonlinear Interactions Between Respiration and Heart Rate: Classical Physiology or Entrained Nonlinear Oscillators", IEEE, pp: 299–300 (1989).

Garrigue, et al., "Night Atrial Overdrive with DDD Pacing Results in a Significant Reduction of Sleep Apnea Episodes and QOL Improvement in Heart Failure Patients", NASPE (2001).

Balaban, et al., "Feasibility of Screening for Sleep Apnea Using Pacemaker Impedance Sensor", PACE, vol. 24, Part II, No. 313, pp: 617 (Apr. 2001).

Bornzin, et al., "Adjusting Heart Rate During Sleep Using Activity Variance", PACE, vol. 17, Part II, pp: 1933–1938 (Nov. 1994).

Garrigue S., Bordier P., Jais P., et al. "Benefit of Atrial Pacing in Sleep Apnea Syndrome," *New England Journal of Med.*, 2002; 346: pp. 404–412.

Balaban, K., Cho Y., Mongeon L., et al. "O2 Saturation During Sleep Correlates Significantly With Pacing Lower Rate in Patients With Sleep Apnea," *PACE* 2002; 25 (Park II): p. 658, No. Abstract No. 544.

* cited by examiner

STIMULATION DEVICE FOR SLEEP APNEA PREVENTION, DETECTION AND TREATMENT

CROSS-REFERENCE TO RELATED APPLICATIONS

This application is related to copending, commonly-assigned U.S. patent application Ser. No. 10/077,053, titled SLEEP APNEA THERAPY DEVICE USING DYNAMIC OVERDRIVE PACING; and U.S. patent application Ser. No. 10/077,660, tilted CARDIAC STIMULATION DEVICE INCLUDING SLEEP APNEA PREVENTION AND TREATMENT; both applications filed concurrently herewith.

FIELD OF THE INVENTION

The present invention relates to techniques for providing therapy to patients who suffer from sleep apnea.

BACKGROUND OF THE INVENTION

Sleep apnea is the cessation of breathing for a short time while sleeping. Sleep apnea has multiple classifications based on source of dysfunction. Obstructive sleep apnea results from mechanical blockage of the airway, for example due to weight of fatty neck tissue compressing the trachea. Central sleep apnea results from neurological dysfunction. Mixed sleep apnea has a combination of mechanical and neurological cause.

Upper airways of the nose and pharynx are held open during breathing by dilator muscles that counteract pressure gradients that would otherwise cause airway collapse. In obstructive sleep apnea, mechanical airway obstruction resulting from superior airway size reduction, increase in airway compliance, and reduction in airway muscle tone leads to pressure disequilibrium that tends to collapse the airways.

The nervous system controls activity of the dilator muscles and respiratory muscles, resulting in a coordinated response to stimulation or depression. Ventilatory fluctuations of hyperventilation and hypoventilation occur during sleep to facilitate breathing without conscious control, reducing the work required for breathing. Unfortunately, in obstructive sleep apnea the ventilatory fluctuations allow superior airway instability and oropharyngeal obstruction, exacerbating the difficulties and dangers of sleep apnea.

Similarly, nervous system interactions of respiratory and cardiovascular functions tend to worsen the problems that arise in sleep apnea. Cardiac arrhythmia conditions such as bradycardia, tachyarrhythmia, atrioventricular block, and ventricular extrasystole are aggravated by obstructive sleep apnea, stimulating the autonomic nervous system and further degrading respiratory performance.

Central sleep apnea is cessation of breathing due to neurological dysfunction, for example a failure to generate neuro-muscular stimulation required to initiate and control a respiratory cycle. The neurological dysfunction are believed to originate in the Thalmus area of the brain and may involve primary brainstem medullary depression resulting from a tumor of the posterior fossa, poliomyletis, or idiopathic central hypoventilation. During a central sleep apnea episode, a patient may fail to breath for an extended time, for example a few seconds up to two or more minutes, then rapidly inhale, typically upon arousal from sleep.

FIG. 11 is a graph that illustrates the mechanism of sleep apnea by correlating ventilatory effort to arterial partial pressure of carbon dioxide ($PaCO_2$). Ventilatory effort is generally greater during waking conditions than while asleep. Onset of sleep results in two phenomena. First, the onset of sleep causes an increased threshold 810 for blood carbon dioxide concentration. Second, gain or slope ($\Delta V/\Delta PaCO_2$) of the ventilatory effort increases. The increase in $PaCO_2$ threshold during sleep allows one to breathe a smaller volume of air. During sleep apnea, collapse of ventilation airways causes a decrease in arterial oxygen concentration ($PaO_2$). Arousal from sleep caused by body defense mechanisms increases upper airway muscle tone, causing the airway to open and arterial oxygen concentration to increase, thereby satisfying body oxygen requirements but setting the stage for a subsequent apnea episode.

Symptoms of sleep apnea include snoring, breath holding during sleep, rapid awakening with gasping for air, morning headaches, depression, irritability, loss of memory, lack of energy, high risk of automobile and workplace accidents, and lack of high quality sleep and resulting daytime grogginess and sleepiness.

Sleep apnea is rarely fatal but is linked to high blood pressure and increased probability of heart disease, stroke, and arrhythmias. Patients with coronary artery disease who have a blood oxygen level lowered by sleep-disordered breathing may be at risk of ventricular arrhythmia and nocturnal sudden death. Furthermore, sleep-disordered breathing may cause coronary artery disease and hypertension.

Various treatments exist for sleep apnea including medical device treatments, surgery, and drugs. The type of treatment depends on the type of sleep apnea and, for obstructive apnea, the type and location of airway obstruction and the patient's health condition. Obstructions can occur in the nose or pharynx. Obstructions in the nose may result from a deviated septum or swollen nasal passages. Obstructions in the upper pharynx may result from enlarged adenoids, long soft palate, large uvula, or large tonsils. Obstructions in the lower pharynx may result from a large or posterior-placed tongue, short jaw, or short and wide neck. Drug therapy is usually sufficient for sleep apnea treatment.

Device treatments may be separated into air pressure devices and neural stimulation devices.

The most common pressure device treatment is termed continuous positive airway pressure (CPAP) and utilizes a mask worn over the nose while sleeping. A hose connects the mask to an air pump that supplies a constant controlled air pressure to a patient's nasal passages and the trachea, preventing collapse. CPAP supplies a continuous, stable pre-determined volume of air to the nasal mask to prevent the airway passage from collapsing.

Bi-level positive airway pressure (BiPAP) treatment is related and similar to CPAP except that BiPAP allows for a reduction in airflow pressure that occurs during expiration. BiPAP allows setting of two different airway pressure levels to avoid fighting incoming air pressure in the expiration portion of the respiratory cycle.

Effectiveness of CPAP varies greatly. Some believe that CPAP is an effective treatment for sleep apnea, but is inconvenient and bothersome to use. Others believe CPAP offers little help in sleep apnea treatment. Still others relate that CPAP is harmful and actually causes sleep apnea episodes since the lung is forced into a constant elevated positive pressure. Normally the lung pressure oscillates between a negative and positive pressure.

Another problem with CPAP and BiPAP devices is the inherent inconvenience and burden of wearing a constricting mask for the sleeping hours, resulting in poor patient compliance with a treatment program.

Various neural stimulation devices are known that generate and apply electrical signals that stimulate nerves to recruit upper airway muscles and maintain muscle tone in the upper airways. Several types of sensing have been used to determine appropriate timing for delivery of muscle stimulation including monitoring of inspiratory effort, respiratory functioning, breathing through the nostrils, and electrical activity associated with contractions of the diaphragm. Problems with neural stimulation include the difficulty of ensuring stimulation of correct muscular structures in the upper airways of a particular patient since the hypoglossal nerve is nearby other structures which should not be stimulated with the structures located differently in different patients.

In addition to device treatments for sleep apnea, various surgical treatments are available. Uvulopalatopharyngoplasty (UPPP) surgery removes fleshy tissue of the uvula and tightens soft tissue of the palate and pharynx in an effort to reduce or remove tissue responsible for obstruction. Unfortunately, UPPP involves significant surgical risks including airway swelling, bleeding, considerable pain for days or weeks, and depression of breathing reflex due to application of general anesthetic, a substantial problem for sleep apnea patients with difficulty breathing while not under anesthesia. Furthermore, effectiveness rates for UPPP are low, on the order of 50% effectiveness in about 50% of patients undergoing the operation.

Laser-assisted uvulaplasty (LUAP) is a laser surgery on the uvula and soft palate that is reported to reduce snoring, but having no controlled studies that show effectiveness in reducing sleep apnea. A major problem with LUAP is that snoring is known not merely as a symptom of sleep apnea, but also as a warning sign of a sleep apnea episode. By silencing the warning provided by snoring, a patient may continue with untreated sleep apnea which may worsen but be ignored.

Pharmaceuticals and medicines are also known treatments for sleep apnea. For example, anti-depressants such as protriptyline or depressants such as klonopin are sometimes prescribed for sleep apnea but appear to be marginally effective.

As a person falls into sleep, muscle tone softens and the weight of body tissues in the vicinity of the upper airway overcomes the structural support of the muscle, causing the airway to collapse. The inspiration-expiration cycle of the collapsed airway does not meet the body's metabolic demand of oxygen intake and carbon dioxide removal.

When the oxygen saturation is satisfactory, the person enters a sound sleeping state, creating the possibility of airway collapse. If an airway collapse occurs, the body oxygen concentration decreases and carbon dioxide concentration increases, activating body defense reflexes and waking the person. Arousal restores upper airway muscle tone, restoring breathing and satisfying oxygen requirements, but setting another cycle of apnea and hyperventilation.

In sleep apnea, oxygen and carbon dioxide concentrations are oscillatory and out of phase by about 180° so that the concomitant sleep state is fragmented, alternating between sleep and arousal.

SUMMARY OF THE INVENTION

A stimulation device and operating method elevate pacing rate to prevent or terminate sleep apnea by increasing cardiac output. Increased cardiac output increases blood oxygen concentration while decreasing carbon dioxide concentration, improving blood gas concentration. In some embodiments, a stimulation device and operating method supply neurostimulation to restore upper airway muscle tone. Improvement in airway muscle tone improves patient condition by increasing capacity for oxygen storage.

In accordance with an embodiment of the present invention, an implantable cardiac stimulation device comprises a metabolic demand sensor, an activity sensor, and one or more pulse generators. The metabolic demand sensor and activity sensor can sense metabolic demand and physical activity parameters, respectively. The pulse generators can generate cardiac pacing pulses with timing based on a comparison of the metabolic demand and physical activity parameters. The elevated cardiac pacing pulse rate can prevent a sleep apnea condition.

In accordance with another embodiment of the invention, an implantable cardiac stimulation device comprises a metabolic demand sensor, an activity sensor, one or more pulse generators, and a neurostimulator. The metabolic demand sensor and activity sensor can sense metabolic demand and physical activity parameters, respectively. The pulse generators can generate cardiac pacing pulses with timing based on a comparison of the metabolic demand and physical activity parameters. Delivery of the timed cardiac pacing pulses can treat a first level of a sleep apnea condition. The neurostimulator is capable of increasing softened upper respiratory muscle tone by recruiting more muscles, thereby maintaining airway patency, treating a second level of sleep apnea.

Suitable metabolic demand parameters for controlling prevention and treatment of the pacing rate include the QT interval, respiration rate, venous oxygen saturation, stroke volume, venous blood temperature, respiration including rate, amplitude, and minute volume, and others.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

DESCRIPTION OF THE EMBODIMENT(S)

The following describes the best mode presently contemplated for practicing the invention. The description is not to be taken in a limiting sense but is set forth to convey the general principles of operation and structure of the illustrative embodiments. The issued claims define the invention scope. In the following description, like numerals or reference designators refer to like parts or elements throughout.

Figure 1A:
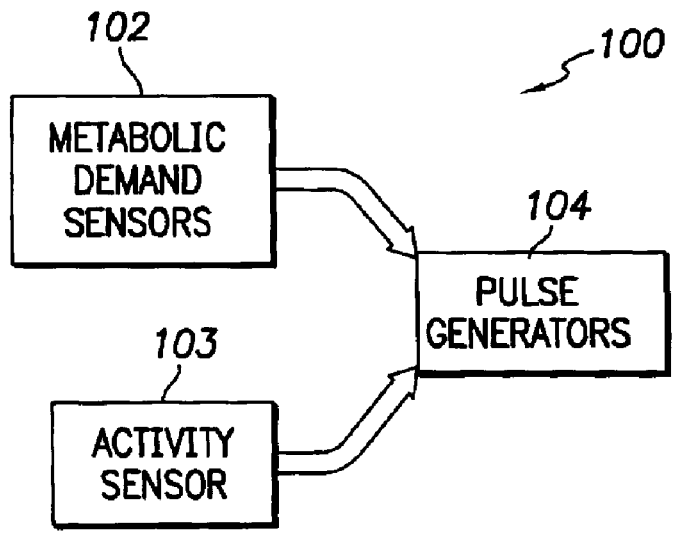
FIGS. 1A and 1B are highly schematic block diagrams that depict examples of implantable cardiac stimulation devices including a metabolic demand sensor, an activity sensor, and one or more pulse generators.
Figure 1B:
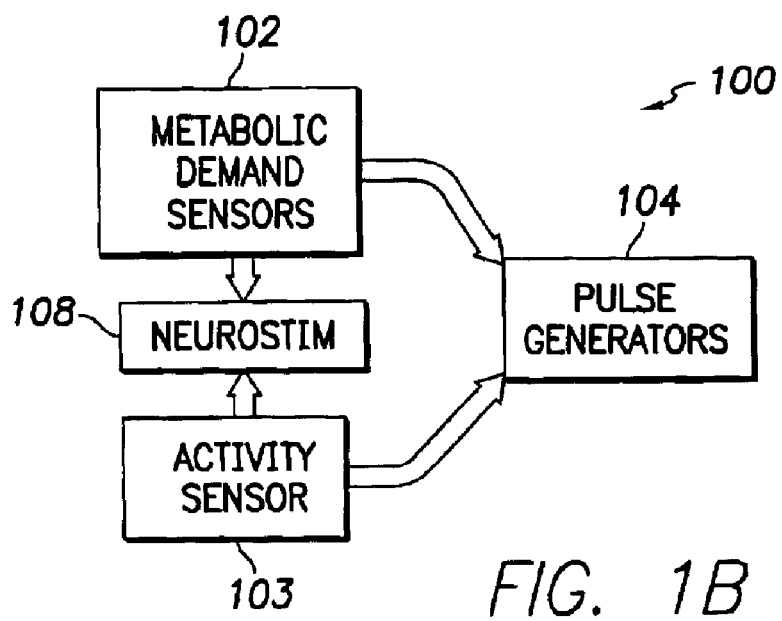

Referring to FIG. 1, a highly schematic block diagram depicts an example of an implantable cardiac stimulation device 100 that includes a metabolic demand sensor 102, and activity sensor 103, and one or more pulse generators 104. The physiological sensor 102 is capable of sensing a metabolic demand parameter such as respiration, minute ventilation, cardiac conductivity, blood oxygen concentration, stroke volume, and others. Still other suitable parameters include parameters based on sensing of cardiac electrical signals, the parameters including QT interval, evoked response integral, stroke volume, paced depolarization integral (PDI), and others. Typically, respiration, minute ventilation, and tidal volume are measured using an impedance sensor.

Various sensors are known to those having ordinary skill in the art that may be used to measure blood oxygen and/or blood carbon dioxide concentration. Fiber optic $PCO_2$ sensors and $PO_2$ sensors are known that are suitable for blood concentration measurements. One example is a combined Clark-type PO2/Stow-Severinghaus type PCO2 sensor for sensing both $PaO_2$ and $PaCO_2$. Other sensors include gel polymeric electrodes that contain a suitable electrolyte for measuring a selected parameter such as $PCO_2$, $PO_2$, or pH. Various other sensors may be suitable including optical fiber pH sensors, optical fiber $PCO_2$ sensors, thermocouple temperature sensors. Suitable $PO_2$ sensors may be electrochemical $PO_2$ sensors or a fluorescent $PO_2$ sensors.

The activity sensor 103 is typically an accelerometer, piezoelectric crystal, or the like, and senses activity and/or activity variance. The pulse generators 104 are configured to generate cardiac pacing pulses with timing based on a comparison of the metabolic demand and physical activity parameters. Analysis of the metabolic demand parameter in comparison with the activity parameter is an indication of the state of the patient. In particular, a reduction over time in both the metabolic demand parameter and the activity parameter is indicative of a sleep state. The pulse generators 104 increase pacing rate during the sleeping state to prevent sleep apnea. The timed cardiac pacing pulses generally prevent a sleep apnea condition by pacing at a rate that is greater than the patient's intrinsic rate while sleeping. The elevated pacing rate tends to prevent the occurrence of sleep apnea. The elevated pacing rate prevents or terminates sleep apnea by increasing cardiac output. Increased cardiac output increases blood oxygen concentration while decreasing carbon dioxide concentration, improving blood gas concentration.

In a more specific example, a cardiac stimulation device 100 can be configured to pace a patient's heart according to a rest mode of operation. In the rest mode, the physiological sensor 102 may be used to determine a suitable heart rate based on the patient's metabolic demand and level of activity at any time. When the patient is awake but not undergoing physical or psychological stress, the cardiac rate is set to a suitable average rate for the resting level of activity. The resting rate is typically set according to various calibrated parameters that can be programmed by a health care worker or can be automatically determined. When the physiological sensor detects a higher level of metabolic demand or physical activity, either or both the metabolic demand sensor 102 or the activity sensor 103 detects the increased demand and generally sets a higher pacing rate. Conversely, when the metabolic demand sensor 102 and/or the activity sensor 103 detects that the patient is sleeping, pacing rate is set to a sleeping rate. For individual cardiac cycles, a base rate is set, typically to an exercise rate, a resting rate, and a sleeping rate, although other rates may be utilized. The heart is paced at the base rate unless the cardiac stimulation device detects an intrinsic heartbeat prior to the time a pacing pulse is to be delivered.

In a device that is configured to prevent, detect, and terminate sleep apnea, the sleeping rate is set higher than the resting rate to prevent sleep apnea. The particular rate to prevent sleep apnea may be set based on the metabolic demand sensor measurement, the activity sensor measurement, or a combination of both measurements.

In addition to preventing sleep apnea, the cardiac stimulation device 100 may detect episodes of sleep apnea using the physiological sensor 102 and invoke a treatment for sleep apnea. One sleep apnea treatment involves pacing the heart at a rate that is at least partly dependent on information from the metabolic demand sensor and the activity sensor.

Some embodiments of the cardiac stimulation device 100 include a implantable neurostimulator 108 that can be implanted to stimulate various nerves and muscles for respiration. Another sleep apnea treatment involves generation of pulses by the neurostimulator 108 to stimulate contraction and expansion of the upper airways or diaphragm. Neurostimulation restores upper airway muscle tone, improving airway muscle tone and patient condition by increasing capacity for oxygen storage.

In one example, the cardiac stimulation device 100 generates cardiac pacing pulses as a rate higher than the intrinsic rate during sleep, and raises the pacing rate upon detection of a sleep apnea condition to attain a first level of sleep apnea treatment. If the first level of treatment is unsuccessful, the cardiac stimulation device 100 stimulates respiratory muscles in a second level of sleep apnea treatment.

Figure 2:
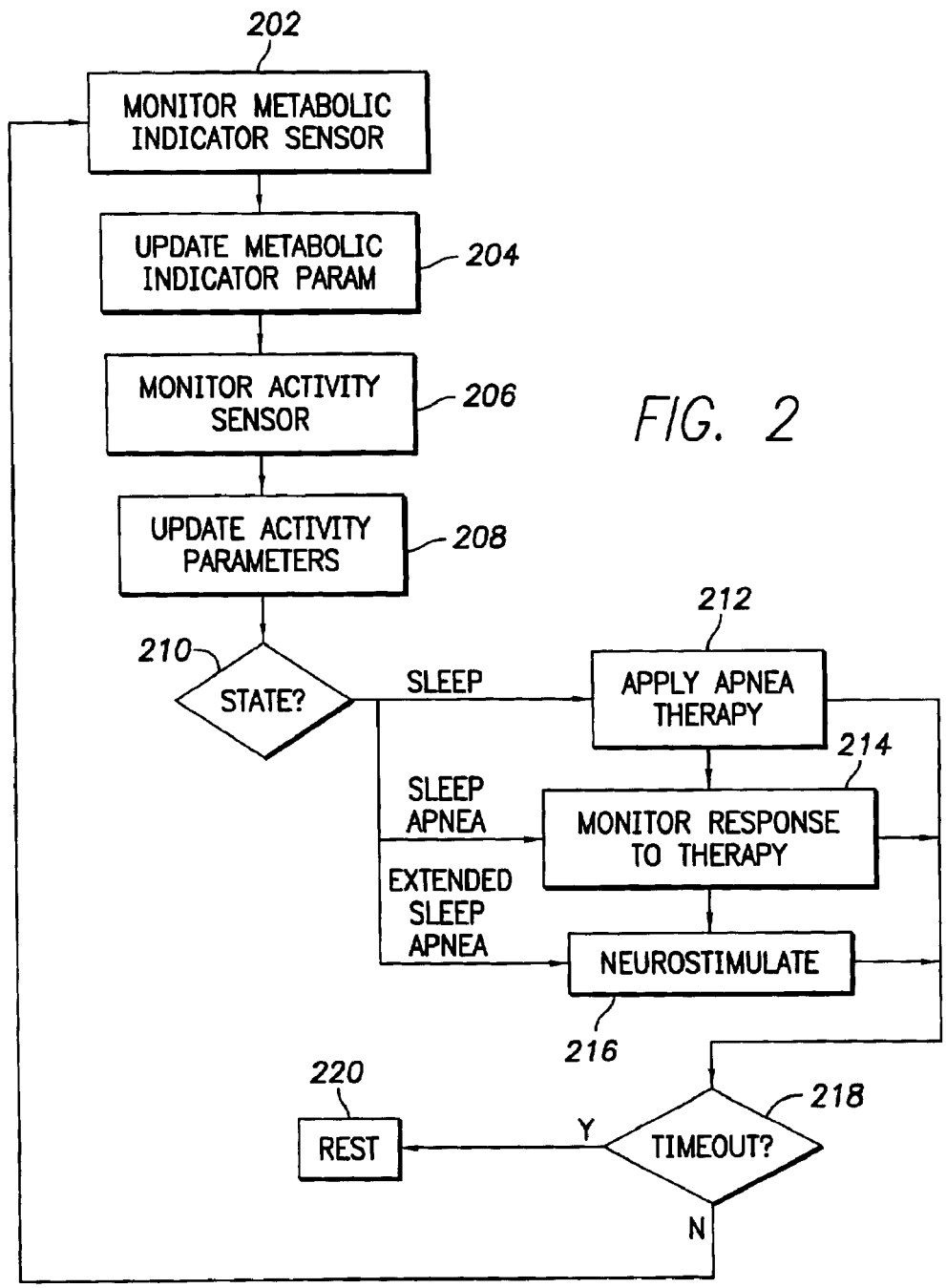
FIG. 2 is a schematic flow chart that illustrates actions of an implantable stimulation device with metabolic and activity sensors and a capability to prevent, detect, and treat sleep apnea.

Referring to FIG. 2, a schematic flow chart illustrates actions of the implantable cardiac stimulation device 100 with metabolic demand 102 and activity 103 sensors and a capability to prevent, detect, and treat sleep apnea. The flow chart describes an overview of the operation and features implemented in one embodiment of the device. In the flow chart, and the additional flow charts described herein, the various acts are summarized in individual actions. The actions or decisions are performed as the operation proceeds. Where a processor or equivalent element is employed, flow charts may describe operations of a control program or executable control logic that may be used by such a processor or equivalent element to effectuate desired control of the stimulation device. Those having ordinary skill in the art can readily write such a control program based on the flow charts and other descriptions presented herein.

The cardiac stimulation device repetitively monitors a metabolic indicator sensor 202 and continually updates one or more metabolic indicator parameters 204. In one example, the metabolic indicator sensor is an impedance sensor and metabolic indicator parameters may include respiration rate, tidal volume, minute volume, respiration signal amplitude, and the like. Generally, updating the metabolic indicator parameters 204 includes filtering to determine relative metabolic demand changes over time.

In another example, a cardiac stimulation device measures oxygen and/or carbon dioxide concentration to detect sleep apnea. In some devices impedance, $PaCO_2$, and $PaO_2$ are measured to detect sleep apnea.

Analysis of the respiration signal may be used to diagnose respiratory disorders. For example, a normal respiratory effort waveform has repetitive inspiratory peaks that are approximately the same amplitude. In contrast, on the onset of apnea, the inspiratory peaks rapidly decrease in amplitude due to increased inspiratory effort in response to difficulty in breathing through the obstructed airway.

During repetitive monitoring of the metabolic indicator sensor, the cardiac stimulation device also repetitively monitors an activity sensor 206 and continually updates one or more parameters indicative of physical activity 208. In one example, the activity sensor is an accelerometer and activity parameters include an instantaneous activity measurement and an activity variance parameter. The activity updating action 208 typically includes filtering to determine relative activity and activity variance changes over time. Typically, the accelerometer is sampled when the signal exceeds a threshold level, at regular timed intervals, or at intervals timed according to the cardiac cycle, although other sampling schemes are possible.

In a detect state action 210, the metabolic indicator and activity parameters are analyzed in combination to determine a patient state, for example from among sleeping, waking, resting, and exercise states. In one example, if either the metabolic indicator or activity parameters are below a rest or sleep threshold, then the patient is determined to be in a rest state or sleep state, respectively. In another example, if both the metabolic indicator and activity parameters are below the rest or sleep threshold, then the patient is determined to be in a respective rest state or sleep state.

In periods of physical activity, both the metabolic indicator and activity parameters generally have increased values, with some differences in responsiveness, indicative of an exercise state. Typically, the pacing rate is increased in an exercise state. For example, the pacing rate may be set to the greater rate of a metabolic indicator-responsive rate and an activity-responsive state.

The activity measurement may be used to more specifically detect sleep apnea in combination with measurement of another parameter such as impedance, $PaCO_2$, or $PaO_2$. The activity measurement makes sleep apnea detection more specific by more particularly identifying the rest condition.

Divergence in the metabolic indicator and the activity parameters is indicative of a sleep apnea condition, both predictive of a sleep apnea condition that has not yet begun and indicative of a current sleep apnea condition. This divergence can be used to prevent, detect, and terminate the sleep apnea condition. In one example, an increased metabolic demand parameter such as minute volume and a simultaneous decrease in the activity parameter can predict the potential for sleep apnea onset. In another example, an elevated level of carbon dioxide and a decrease in sensed activity indicates a sleeping state. In a further example, an impedance sensor is used to detect sleep apnea.

The cardiac stimulation device controls pacing pulse generation depending on the patient's state, such as sleep, waking, rest, exercise, onset of sleep apnea, and sleep apnea. In one example, for prevention and treatment of sleep apnea the device increases the base rate while sleeping 212. In one specific example, the stimulation device may increase the resting rate to the base rate. For the onset of sleep apnea, the stimulation device may increase the pacing rate a further amount. Upon detection of a current sleep apnea condition, the device increases the pacing rate even further.

If the patient enters a sleep apnea condition, the stimulation device analyzes the response to the treatment 214, typically by determining the duration of the condition, duration of the treatment, and by continuing to monitor the metabolic indicator and activity parameters to detect improvements or declines in condition.

If warranted, the device can begin a higher level of sleep apnea treatment, for example by neurostimulating 216 respiratory nerves or muscles. For example, some devices treat sleep apnea by elevating the pacing rate and, if sleep apnea persists despite the pacing therapy, the device delivers neural stimulation. In another operating mode, a stimulation device delivers pacing to prevent sleep apnea, or bypasses pacing and delivers neural stimulation.

The primary and secondary levels of sleep apnea treatment are typically timed 218 and terminated if treatment does not remedy the condition. The actions may be repeated after a resting period 220.

The device can control neurostimulator pulse timing based on signals from the metabolic sensor. For example, a respiration sensor generates an analog waveform indicative of respiratory effort and having suitable markers to allow management of sleep apnea diagnosis and neurostimulation therapy. The respiration sensor generates a waveform that is characterized by a negative peak on completion of expiration, a positive peak on completion of inspiration, and a turning point indicative of inspiration onset. Respiration signal morphology allows classification of various phases and events including respiratory pause, inspiratory phase, and expiratory phase. The neurostimulator can be controlled to synchronize pulses with the respiratory cycle.

In one operating mode, the stimulation device may treat sleep apnea by stimulating muscle that holds the airway open in synchrony with the inspiratory respiration phase. The muscle to be stimulated may be selected based on various considerations including position of the obstruction and structure of the patients' airways, muscle, and nerves. The stimulated muscle may be an upper airway muscle such as the genioglossus muscle stimulated by a cuff electrode placed around the hypoglossal nerve, or other upper airway muscles or nerves that produce a similar action. Other muscles in the upper oro-pharyngeal and/or naso-pharyngeal airway that may be suitable for treatment of sleep apnea include one or more of the geniohyoid, genioglossus, digastric, stylopharyngei or mylohyoid muscles.

Alternatively, nerves or muscles separate from the upper airway, such as the diaphragm and other accessory muscles including the intercostal muscles, sternomastoid muscles, or around the nerves responsible for stimulation of the respiratory muscles, may be stimulated to treat sleep apnea or other respiratory disorders. In a manner known to those having ordinary skill in the art, phrenic nerve stimulation or diaphragmatic pacing utilizes electrical stimulation to regulate and control the patient's diaphragm which is innervated bilaterally by the phrenic nerves to assist or support ventilation.

Several treatments for sleep-apnea syndrome are known to those having ordinary skill in the art and involve generation of electrical signals to stimulate nerves that activate a patient's upper airway muscles, thereby maintaining upper airway patency. Some stimulation treatments deliver electrical bursts transcutaneously from electrodes mounted external to the patient's body to nerves innervating upper airway muscles. Other treatments utilize electrodes inserted directly into musculature of the upper airway. For example, electrodes may be inserted to trigger stimulation of the genioglossus muscle. In a specific example, an intraoral, sublingual electrode can be used to electrically stimulate the genioglossus muscle to maintain upper airway patency.

In other examples, the cardiac stimulation device may use different metabolic demand and activity sensors to prevent, manage, detect, and treat sleep apnea. Metabolic demand sensors that are useful to detect a sleep condition include sensors that detect characteristics of cardiac electrical polarization, and other types of sensors. For example, a physiological sensor that measures QT interval may detect a sleep condition as a prolonged QT interval. A sensor of cardiac conductivity detects sleep as a depression in conductivity. Evoked response integral amplitude decreases during sleep while the evoked response duration increases. Cardiac contractility is reduced during sleep. Stroke volume increases when a patient is supine. A sensor of paced depolarization integral (PDI) is depressed during sleep. Blood oxygen concentration decreases in obstructive sleep apnea conditions. The cardiac stimulation device is capable of detecting sleep apnea episodes based on abnormal breathing using any sensor.

Figure 3:
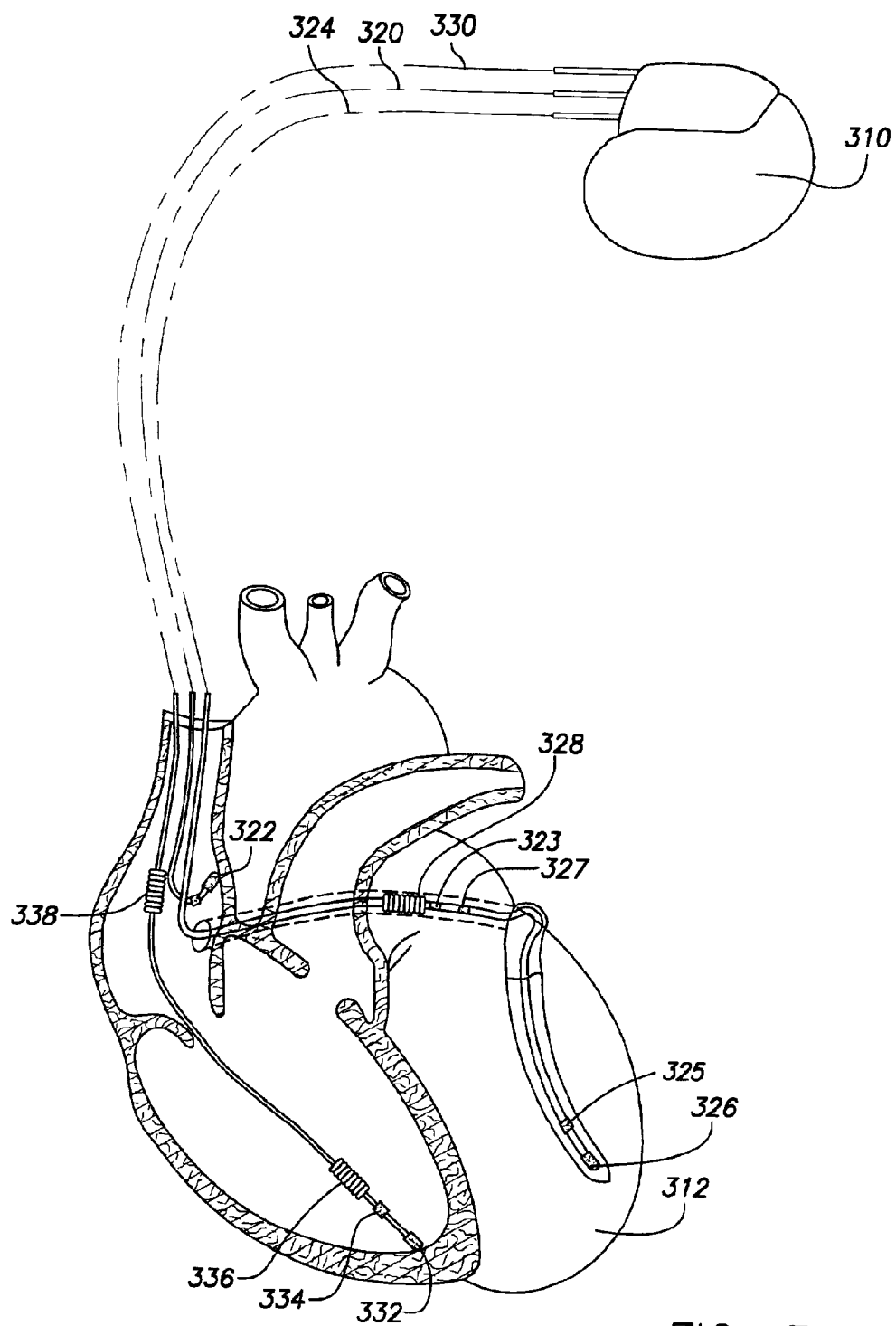
FIG. 3 is a simplified diagram illustrating an implantable stimulation device in electrical communication with at least three leads implanted into a patient's heart for delivering multi-chamber stimulation and shock therapy.

Referring to FIG. 3, a stimulation device 310 electrically couples to a patient's heart 312 using three leads 320, 324, and 330 to electrically communicate signals suitable for delivering multiple-chamber stimulation and shock therapy. The stimulation device 310 couples to an implantable right atrial lead 320 having at least an atrial tip electrode 322 to sense atrial cardiac signals and to supply right atrial chamber stimulation therapy. The atrial tip electrode 322 typically is implanted in the patient's right atrial appendage.

The stimulation device 310 is coupled to a "coronary sinus" lead 324 to sense left atrial and ventricular cardiac signals and to supply left chamber pacing therapy. The "coronary sinus" lead 324 is designed for placement in the "coronary sinus region" for positioning a distal electrode adjacent to the left ventricle and/or additional electrode(s) adjacent to the left atrium. The phrase "coronary sinus region" refers to the vasculature of the left ventricle including any portion of the coronary sinus, great cardiac vein, left marginal vein, left posterior ventricular vein, middle cardiac vein, and/or small cardiac vein or any other cardiac vein accessible by the coronary sinus.

The lead 324 may be used to supply stimulation pulses to a patient's left ventricle in biventricular pacing systems. Patients with chronic atrial fibrillation may be treated using biventricular VVIR pacemakers with left ventricular 324and right ventricular 330 leads connected to the stimulation device 310. In patient's with spontaneous sinus rhythm, biventricular DDDR stimulating devices may be implanted with an atrial lead 320 placed in the upper right atrium and two ventricular leads 324 and 330 connected to the left and right ventricles, respectively.

An illustrative coronary sinus lead 324 is configured to receive atrial and ventricular cardiac signals and to deliver left ventricular pacing therapy using at least a left ventricular tip electrode 326. The coronary sinus lead 324 delivers left atrial pacing therapy using at least a left atrial ring electrode 327. The coronary sinus lead 324 delivers shocking therapy using at least a left atrial coil electrode 328. U.S. patent application Ser. No. 09/457,277, filed Dec. 8, 1998, entitled "A Self-Anchoring, Steerable Coronary Sinus Lead" (Pianca et al.); and U.S. Pat. No. 5,466,254, "Coronary Sinus Lead with Atrial Sensing Capability" (Helland), that are hereby incorporated herein by reference, contain a complete description of a suitable coronary sinus lead.

FIG. 3 shows the stimulation device 310 electrically coupled with the patient's heart 312 by an implantable right ventricular lead 330. The right ventricular lead 330 in the illustrative embodiment has a right ventricular tip electrode 332, a right ventricular ring electrode 334, a right ventricular (RV) coil electrode 336, and an SVC coil electrode 338. Typically, the right ventricular lead 330 is transvenously inserted into the heart 312 to place the right ventricular tip electrode 332 in the right ventricular apex, positioning the RV coil electrode 336 in the right ventricle and the SVC coil electrode 338 in the superior vena cava. Inserted in this manner, the right ventricular lead 330 is capable of receiving cardiac signals and delivering stimulation in the form of pacing and shock therapy to the right ventricle.

Figure 4:
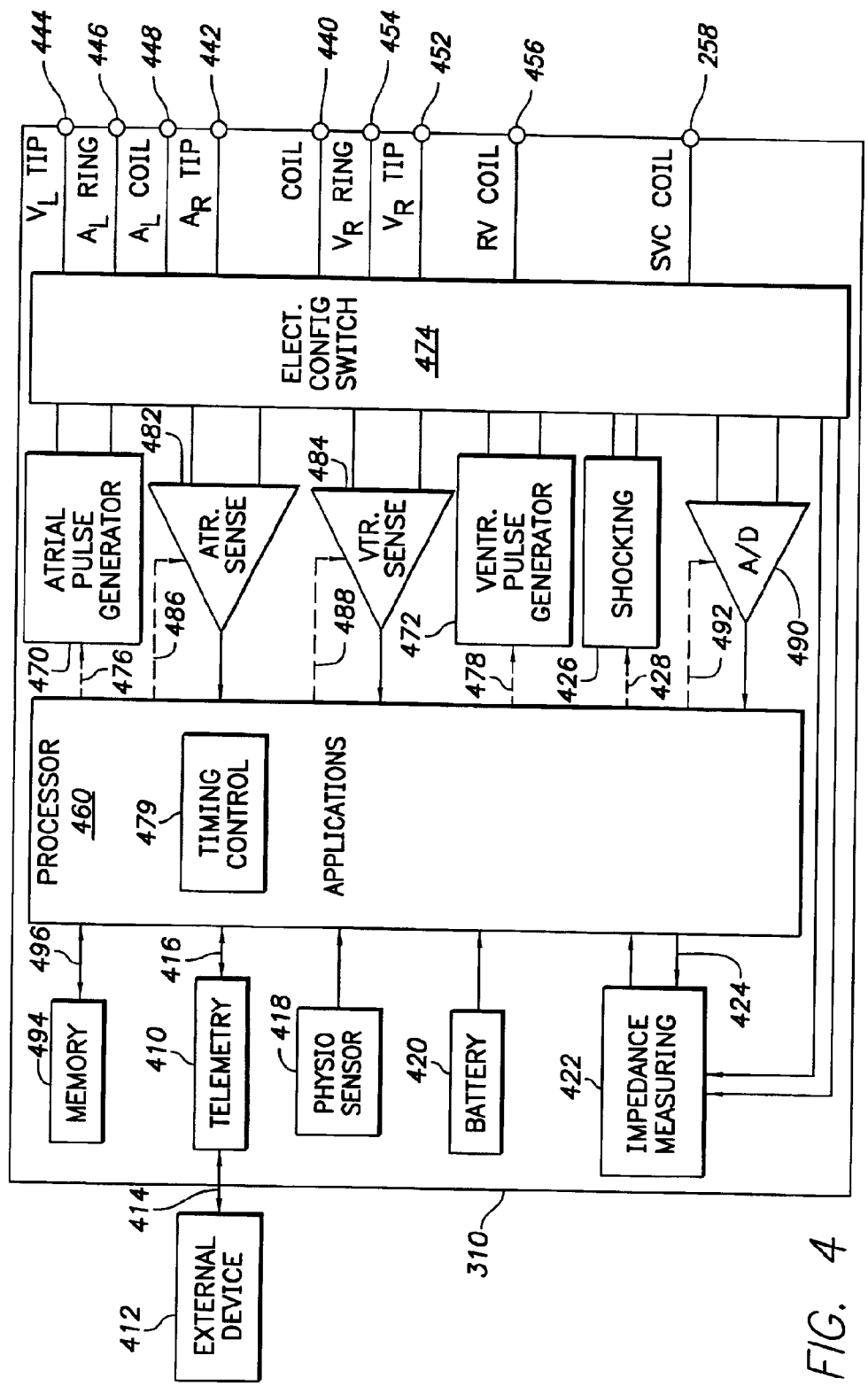
FIG. 4 is a functional block diagram that shows a multi-chamber implantable stimulation device illustrating basic elements of a stimulation device capable of cardioversion, defibrillation and pacing stimulation in four chambers of the heart.

Referring to FIG. 4, a simplified block diagram shows the multiple-chamber implantable stimulation device 310 that is capable of treating both fast and slow arrhythmias with stimulation therapy such as cardioversion, defibrillation, and pacing stimulation. The particular multi-chamber device is shown for illustration purposes only, and one of ordinary skill in the art can readily duplicate, eliminate, or disable various portions of circuitry in any desired combination to produce a device capable of delivering treatment in a desired chamber or chambers. Suitable treatments include, but are not limited to cardioversion, defibrillation and pacing stimulation, in either or both the atria and ventricles.

The housing 440 for the stimulation device 310, shown schematically in FIG. 4, is often referred to as the "can", "case" or "case electrode" and may be selected, for example by programming, to function as a return electrode for all "unipolar" modes. The housing 440 may also or otherwise be used as a return electrode alone or in combination with one or more of the coil electrodes, 328, 336 and 338, for delivering shocking stimulation to tissue. The housing 440 includes a connector (not shown) with a plurality of terminals 442, 444, 446, 448, 452, 454, 456, and 458. The terminals are shown schematically with, for convenience, names of the electrodes that are connected to the terminals shown next to the appropriate terminals. For example, at least a right atrial tip terminal ($A_R$ TIP) 442 is adapted for connection to the atrial tip electrode 322 to perform right atrial sensing and pacing.

To sense, pace, and shock in the left heart chambers, the connector includes at least a left ventricular tip terminal ($V_L$ TIP) 444, a left atrial ring terminal ($A_L$ RING) 446, and a left atrial shocking terminal ($A_L$ COIL) 448. The left ventricular tip terminal ($V_L$ TIP) 444 is adapted for connecting to the left ventricular ring electrode 325. The left atrial ring terminal (A_L RING) 446 is configured to connect to the left atrial tip electrode 323. The left atrial shocking terminal (A_L COIL) 448 is adapted to connect to the left atrial coil electrode 328.

The connector further includes a right ventricular tip terminal (V_R TIP) 452, a right ventricular ring terminal (V_R RING) 454, a right ventricular shocking terminal (R_V COIL) 456, and an SVC shocking terminal (SVC COIL) 458 to support right chamber sensing, pacing and shocking. The right ventricular tip terminal (V_R TIP) 452 is formed to connect to the right ventricular tip electrode 332. The right ventricular ring terminal (V_R RING) 454 is adapted to connect to the right ventricular ring electrode 334. The right ventricular shocking terminal (R_V COIL) 456 can connect to the RV coil electrode 336. The SVC shocking terminal (SVC COIL) 458 is configured to connect to the SVC coil electrode 338.

A programmable processor 460 is contained in the housing 440 and controls the various modes of stimulation therapy. The processor 460 can be implemented as any suitable control device such as a microcontroller, a controller, a microprocessor, a central processing unit, a signal processor, a digital signal processor, a state machine, a control logic, discrete control circuitry, or any similar control circuitry. In some embodiments, the processor 460 is designed specifically for controlling the delivery of stimulation therapy. The processor 460 may include RAM or ROM memory, logic and timing circuitry, state machine circuitry, and I/O circuitry. The processor 460 has a capability to process or monitor input signals or data, typically as a program code that is stored in a designated block of memory and executable by the processor 460. Details of design and operation of the processor 460 are well-known to those having ordinary skill in the art so that any suitable processor 460 may be used that can execute the functions described herein. Usage of microprocessor-based control circuits for performing timing and data analysis functions are well known by those having ordinary skill in the art.

Referring again to FIG. 4, an atrial pulse generator 470 and a ventricular pulse generator 472 generate pacing stimulation pulses that are delivered by the right atrial lead 320, the right ventricular lead 330, and/or the coronary sinus lead 324 via an electrode configuration switch 474. To therapeutically stimulate each of the four heart chambers, the atrial and ventricular pulse generators 470 and 472 may include dedicated, independent pulse generators, multiplexed pulse generators, or shared pulse generators. The processor 460 controls pulse generators 470 and 472 via appropriate respective control signals 476 and 478 to trigger or inhibit the stimulation pulses.

Processor 460 further includes timing control circuitry 479 to control timing of various stimulation pulse events such as pacing rate, atrio-ventricular (AV) delay, atrial interconduction (A-A) delay, or ventricular interconduction (V-V) delay, and others. The processor 460 and timing control circuitry 479 also track timing of refractory periods, blanking intervals, noise detection windows, evoked response windows, alert intervals, marker channel timing, and others. The timing control circuitry 479 times other various delays, event intervals, and timing windows that are well-known to those having ordinary skill in the art.

Switch 474 includes a plurality of switches for connecting the desired electrodes to the appropriate I/O circuits, allowing complete selective programming of electrode configuration. Typically, the processor 460 generates a control signal 480 that configures the switch 474 by selectively setting an appropriate combination of switches (not shown). In one example, the switches determine polarity of the simulation pulses from among possible unipolar, bipolar, combipolar polarities, and the like as are well-known to those having ordinary skill in the art.

Atrial sensing circuits 482 and ventricular sensing circuits 484 can detect cardiac activity in each of the four heart chambers by selective coupling to the right atrial lead 320, coronary sinus lead 324, and the right ventricular lead 330, through switch 474. The atrial (ATR. SENSE) 482 and ventricular (VTR. SENSE) 484 sensing circuits typically include amplifiers of various types such as dedicated sense amplifiers, multiplexed amplifiers, or shared amplifiers. The switch 474 determines sensing polarity of the cardiac signal by selectively configuring appropriate switches in a manner that is known to those having ordinary skill in the art. Stimulation and sensing polarity control is separate so that a clinician may program sensing polarity independently from programming of stimulation polarity.

The sensing circuits 482 and 484 each generally include one or more amplifiers, bandpass filtering, and a threshold detection circuit. Suitable amplifiers are precision amplifiers with programmable gain and/or automatic gain control functionality, a feature well-known to those having ordinary skill in the art. The sensing circuits 482 and 484 are programmed, either manually or automatically using a gain control algorithm to selectively sense a cardiac signal of interest. Automatic gain control enables the device 310 to effectively sense low amplitude cardiac signals, thereby managing the difficult problem of sensing low amplitude signal characteristics that occur in atrial or ventricular fibrillation conditions. Processor 460 receives output signals from atrial and ventricular sensing circuits 482 and 484. Processor 460 responds to the sensing signals by triggering or inhibiting atrial 470 and ventricular 472 pulse generators in the manner of "demand pacing" in response to the absence or presence of cardiac activity in the appropriate heart chambers.

The device 310 performs arrhythmia detection utilizing the atrial and ventricular sensing circuits 482 and 484 to sense cardiac signals. In arrhythmia detection, the device 310 determines whether a rhythm is physiologic or pathologic. As used herein, the term "sensing" refers to monitoring of a cardiac signal for determining the presence of a cardiac pulse. The term "detection" refers to processing of the sensed cardiac signals to determine the presence of an arrhythmia. Processor 460 classifies cardiac signals by comparing timing intervals between sensed events to a predefined rate zone limit and analyzing other characteristics to determine an appropriate remedial therapy. Measured and monitored timing intervals between sensed events include P-waves, R-waves, and depolarization signals associated with fibrillation which are sometimes referred to as "F-waves" or "Fib-waves", such as "atrial Fib-waves" and "ventricular Fib-waves". The timing intervals are compared to a predefined rate zone limit such as bradycardia, normal, low rate VT, high rate VT, fibrillation rate zones, and other rate limits that are known to those having ordinary skill in the art. Other analytical characteristics are selected from among, but not limited to sudden onset, stability, physiologic sensors, and morphology. The device 310 delivers remedial therapies such as bradycardia pacing, anti-tachycardia pacing, cardioversion shocks or defibrillation shocks, collectively referred to as "tiered therapy".

An analog-to-digital (A/D) data acquisition system 490 also receives cardiac signals for acquisition, conversion, and storage or communication. The data acquisition system 490 is configured to acquire intracardiac electrogram signals in analog format, convert the raw analog data into a digital signal, and store the digital signals for later processing and/or telemetric transmission to an external device 412. The data acquisition system 490 couples to the right atrial lead 320, the coronary sinus lead 324, and the right ventricular lead 330 through the switch 474 to acquire cardiac signal samples across any desired pair of electrodes.

The processor 460 is coupled to a memory 494 by a suitable data/address bus 496. Memory 494 stores programmable and/or automatically-determined operating parameters used by the processor 460. Operating parameters are stored, determined, or modified, to customize the operation of the stimulation device 310 to needs of a particular patient. The operating parameters define, for example, pacing pulse amplitude, pulse duration, electrode polarity, stimulation rate, sensitivity, automatic features, arrhythmia detection criteria, and stimulation pulse characteristics. Stimulation pulse characteristics include amplitude, waveshape, and vector of each shocking pulse to be delivered to the patient's heart 312 within particular tiers of therapy.

Operating parameters of the implantable device 310 may be non-invasively programmed into the memory 494 through a telemetry circuit 410 in telemetric communication with the external device 412, such as a programmer, transtelephonic transceiver, or a diagnostic system analyzer. The processor 460 sends a control signal 416 that activates the telemetry circuit 410. The telemetry circuit 410 communicates intracardiac electrograms and status information relating to the operation of the device 310 to the external device 412 through an established communication link 414.

In some embodiments, the stimulation device 310 can include one or more physiologic sensors including a metabolic demand sensor 418 and an activity sensor 419, commonly called a "rate-responsive" sensor that is typically used to adjust pacing stimulation rate according to the exercise state of the patient. The physiological sensor 418 may also be used to detect changes in cardiac output, changes in the physiological condition of the heart, or diurnal changes in activity such as detecting sleep and wake states. The processor 460 responds by adjusting various pacing parameters such as rate, AV Delay, V-V Delay, and the like, at which atrial and ventricular pulse generators 470 and 472 generate stimulation pulses.

Although the example shows the physiological sensor 418 included within the stimulation device 310, the physiologic sensor 418 may otherwise be located external to the stimulation device 310. An external physiological sensor 418 may be implanted within a patient or carried by the patient. A common type of rate responsive sensor is an activity sensor such as an accelerometer or a piezoelectric crystal, mounted within the housing 440 of the stimulation device 310 that generates a measurable electrical potential when a mechanical stress resulting from physical activity is applied to the sensor. By analyzing the signal from a piezoelectric activity sensor, a rate-responsive pacemaker can detect various conditions or determine how frequently pacing pulses should be applied to the patient's heart.

Multiple other types of physiologic sensors are suitable, including for example sensors that measure central venous blood temperature, blood oxygen content, blood pH level, QT time interval, respiration rate and/or minute ventilation, ventricular gradient, and other parameters. Generally any sensor capable of sensing a physiological parameter that corresponds to the exercise state of the patient may be used although aspects of response time, unpredictable emotionally-induced variations, side effects, and performance variability among different patients are important considerations in selection.

Some embodiments may include a "sleep state" or diurnal sensor that can detect sleep and wake states. One diurnal sensor is called an "activity variance" sensor in which an activity sensor is monitored diurnally to detect the low variance in the measurement that corresponds to the sleep state. U.S. Pat. No. 5,476,483 (Bornzin et. al), issued Dec. 19, 1995, provides a complete description of the activity variance sensor.

The stimulation device 310 includes a battery 420 that supplies operating power to all of the circuits shown in the device 310. For a stimulation device 310 that is capable of delivering a shocking therapy, a suitable battery 420 is capable of operating at low current drains for long periods of time, but also be capable of generating high-current pulses for capacitor charging when the patient requires a shock pulse.

The device 310 also has an impedance measuring circuit 422 that is enabled by a control signal 424 from the processor 460. The impedance measuring circuit 422 is useful for one or more of several functions. Impedance measuring circuit 422 is useful for measuring respiration or minute ventilation that can be applied to rate responsive pacing or other automatic control operations. The impedance measuring circuit 422 can be used for many other various operations including measurements of stroke volume, detection of heart value opening, and the like.

In some embodiments, the stimulation device 310 is configured to operate as an implantable cardioverter/defibrillator (ICD) device. An ICD device detects arrhythmia conditions and responds to the detected arrhythmia condition by automatically applying a suitable electrical shock therapy to the heart for the purpose of terminating the detected arrhythmia. The processor 460 controls a shocking circuit 426 by way of a control signal 428. The shocking circuit 426 generates shocking pulses of low (up to 0.5 Joules), moderate (0.5–10 Joules), or high energy (11 to 40 Joules), under control by the processor 460. Shocking pulses are applied to the patient's heart 312 through at least two shocking electrodes, selected from the left atrial coil electrode 328, the RV coil electrode 336, and/or the SVC coil electrode 338. The housing 440 may be used as an active electrode in combination with the RV coil electrode 336, or as part of a split electrical vector using the SVC coil electrode 338 or the left atrial coil electrode 328, for example using the RV electrode as a common electrode.

Cardioversion shock energy is a relatively low to moderate energy level to reduce pain felt by the patient. The cardioversion shock can be synchronized with an R-wave cardiac signal and can be part of tachycardia treatment. Defibrillation shock energy is generally a moderate to high energy level, for example corresponding to thresholds in the range of 5–40 Joules, and is delivered asynchronous with respect to intrinsic cardiac activity since R-waves may be insufficiently organized for synchronous stimulation utility. Defibrillation shocks are applied exclusively to treatment of fibrillation. Processor 460 is capable of controlling the synchronous or asynchronous delivery of the shocking pulses.

The stimulation device 310 may include multiple physiological sensors 418 to sense multiple different physiological parameters. One type of physiological sensor 418 is a metabolic rate sensor that supplies an indication of metabolic demand that is useful for various diagnostic and control functions. One common metabolic rate sensor is a minute ventilation or minute volume sensor that measures a patient's respiration rate and tidal volume. The patient's metabolic demand is indicated by the patient's rate of breathing and the volume of air breathed in a respiratory cycle.

A typical configuration for measuring a minute ventilation signal uses impedance sensing by the ventricular sensing circuit 484 and/or the atrial sensing circuit 482 to periodically measure transthoracic impedance between a lead implanted in the patient's heart and an indifferent electrode, such as the device housing 440. Transthoracic impedance is proportional to chest volume and indicates the degree and rate of patient chest expansion and contraction.

Processor 460 receives a metabolic indicated rate signal from the physiological sensor 418, here a metabolic sensor. The illustrative metabolic sensor includes a minute ventilation sensor that periodically measures the patient's transthoracic impedance. In one example, the metabolic sensor induces delivery of transthoracic measurement pulses from a selected lead of leads 320, 324, and 330 implanted within the heart 312 and measures a return pulse on an indifferent electrode such as the housing 440. Transthoracic measurement pulses can be filtered to remove heart fluctuation components and other noise signals to sense only signals indicative of transthoracic impedance.

Transthoracic impedance is proportional to a minute ventilation or minute volume parameter. Typically, a patient breathes faster and deeper when engaged in a relatively strenuous physical activity that requires greater delivery of oxygenated blood by the heart. Therefore, minute ventilation and minute volume are parameters allowing determination of a metabolic indicated rate.

Transthoracic impedance and minute ventilation may be sampled and measured over a discrete period of time, and the measured value translated into a metabolic indicated rate using algorithms known to those having ordinary skill in the art. The algorithms produce the metabolic indicated rate, a heart rate that is suitable to meet the metabolic demand that corresponds to a particular measured minute ventilation value. Determination of a metabolic indicated rate is disclosed in more detail in U.S. Pat. No. 5,626,622 that is incorporated by reference herein in its entirety.

In the illustrative stimulation device 310, processor 460 also receives signals from a second physiological sensor 418, an activity sensor. In one example, the activity sensor is an acceleration-based activity sensor that generates an activity signal that can be used to derive an activity indicated rate (AIR) parameter. One suitable activity sensor is a piezoelectric sensor that creates an electrical signal in response to accelerating motions of the patient's body.

If acceleration signals are greater than a preset threshold level, the activity sensor digitizes the signal and increments a counter. The activity sensor supplies a count value at periodic intervals. The magnitude of the count value over a selected period represents patient activity and can be translated into the activity indicated rate (AIR) using techniques known to those having ordinary skill in the art.

In a typical system, sleep apnea prevention may be implemented as a control program executed by processor 460. The control program enables stimulation device 310 to generate a pacing therapy such as a rate-responsive pacing therapy and to modulate base pacing rate. The control program may be enabled to switch the base pacing rate from a preprogrammed resting rate to a preprogrammed sleeping rate when the stimulation device 310 detects that the patient has fallen asleep. The control program also may be enabled to switch the base pacing rate from the sleeping rate to the resting rate when the stimulation device 310 determines that the patient is no longer sleeping. If the patient engages in physical activity, the control program may be enabled to cause the stimulation device 310 to increase pacing rate above the resting rate by an amount that accommodates the level of activity as measured by the sensor 418.

A start-up command received from the external programmer 412 through telemetry circuit 410 can activate the control program. The start-up command may be sent one or more times as part of an implantation procedure, and during subsequent follow-up visits.

Figure 5A:
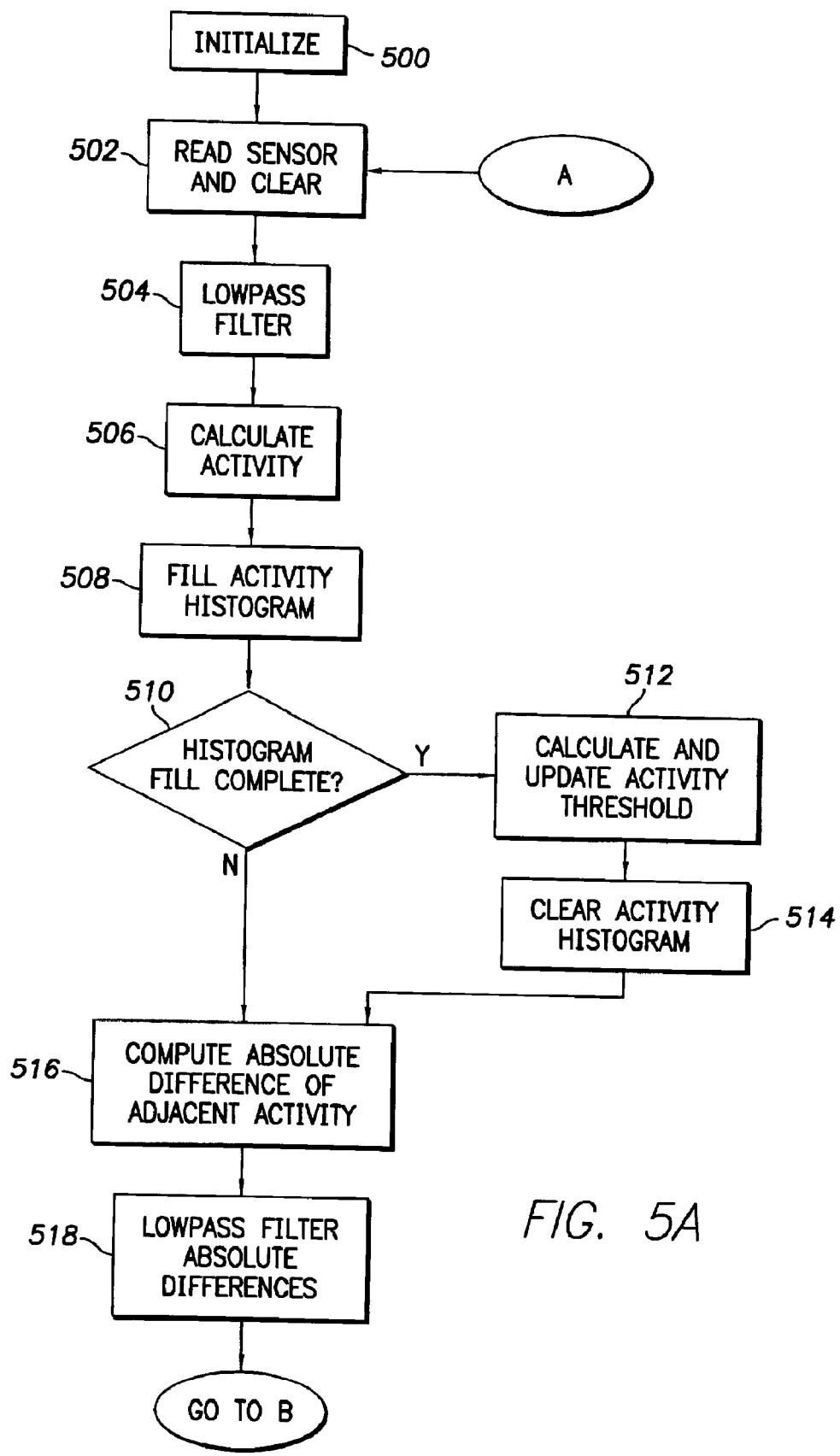
FIGS. 5A and 5B are logic flow diagrams that depict a suitable first example of a control program that modulates base pacing rate in a stimulation device.
Figure 5B:
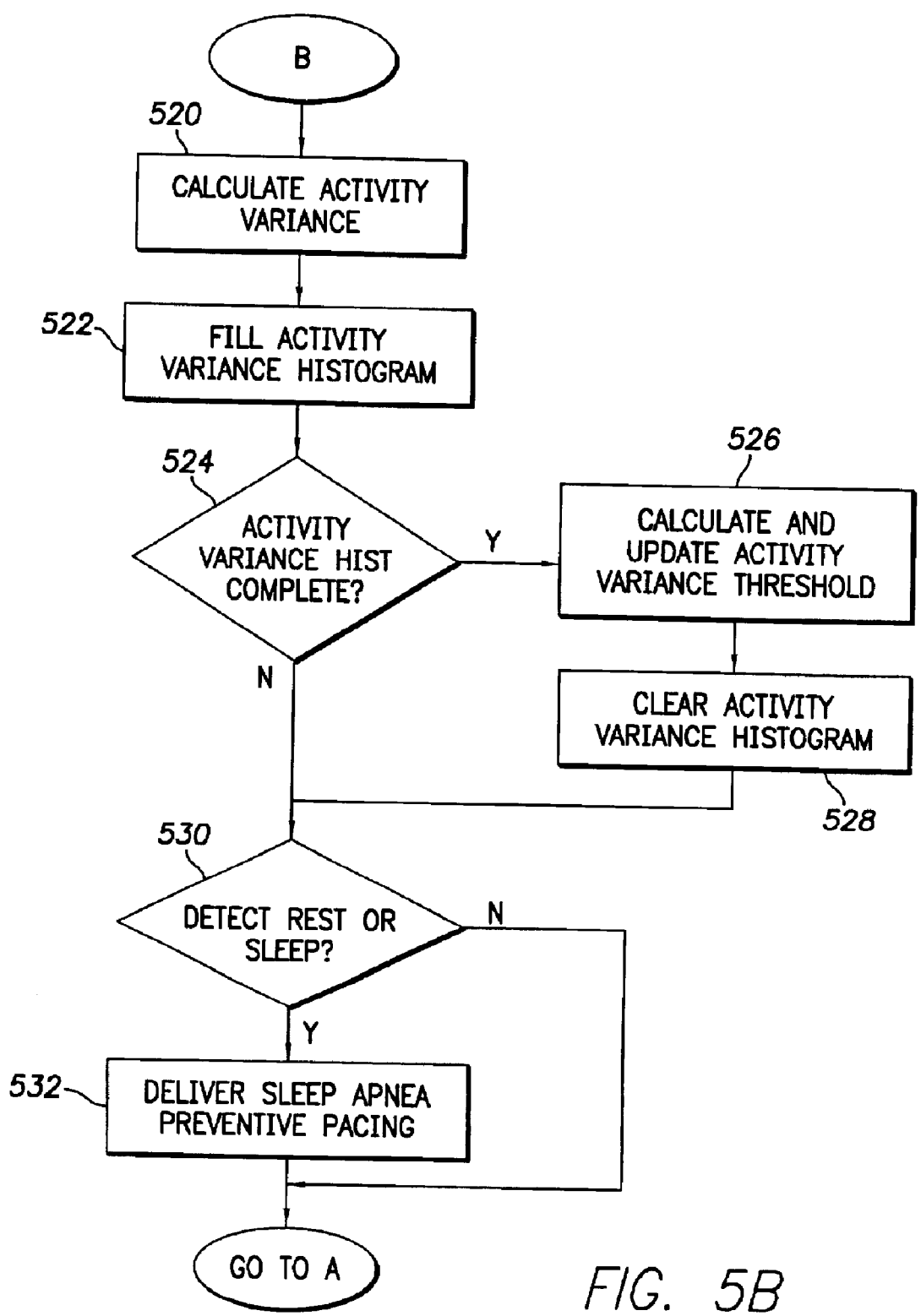

Referring to FIGS. 5A and 5B in conjunction with structures shown in FIG. 4, a logic flow diagram shows an example of a suitable control program for sleep apnea prevention. On receipt of the start-up command, processor 460 executes an initialization action 500 during which external programmer 412 sends operational parameters through the telemetry circuit 410 to the stimulation device 310 for storage in memory 494. The operational parameters include conventional pacing parameters such as pacing rate, pulse width, pulse amplitude, and the like, and special parameters that govern operation of the sensor 418. For example, a health care provider can disable base rate modulation, or entirely disable rate-responsive pacing during initialization action 500.

Parameters for implementing base rate modulation may include sleeping rate (Sleep-Rate), resting rate (Rest-Rate), sleep hours (Sleep-Hrs), activity slope (Act-Slope), and maximum pacing rate (MPR). Sleeping rate generally may be set to comfortably meet a patient's low metabolic demands during sleep, for example 55 bpm for an average patient. Resting rate is a suitable rate for an awake but inactive patient, for example 65 bpm. Sleep hours are set to the number of hours the patient typically sleeps each day, such as 7 hours. Activity slope is set to allow the stimulation device 310 to sufficiently increase or decrease pacing rate as activity level increases or decreases, for example 0.6 bpm/count. After initialization, the processor 460 adjusts activity slope according to the patient's activity profile. Maximum pacing rate is set to safely supply the patient's metabolic demands during high exertion, such as 150 bpm.

After initialization action 500, the processor 460 reads a value from a sensor in read sensor and clear action 502. Typically, processor 460 reads contents of a counter or register (not shown) associated with the sensor 418 and indicative of a sensed value, and stores the value in a variable designated Count-Val. In one example, counter contents digitally represent a patient's activity level measured during a predetermined period, for example 100 ms, within a current heartbeat interval. After reading, read-and-clear action 502 clears the counter in preparation for the next heartbeat interval.

In a lowpass filter action 504, processor 460 may average the current counter reading with one or more previous heartbeat interval counter readings. In one example shown in Equation 1, the most recent sample Count_Val and a preceding sample Count_Val_Old are averaged to avoid influence of uncharacteristically high or low measurements.

$$\text{Count\_Val} = (\text{Count\_Val} + \text{Count\_Val\_Old})/2 \qquad (1)$$

In one example, variable Count_Val_Old stores the counter reading acquired during the previous heartbeat cycle, or the current counter reading immediately after initialization. Alternatively, Count_Val_Old may store a sample that is not immediately preceding or may store an average of previous samples. Some embodiments may utilize Count_Val without averaging.

In a second example of the lowpass filter action 504, processor 460 filters the value stored in Count_Val using a recursive low-pass filter to derive a digitally smoothed representation of the patient's current activity level, as shown by Equation 2:

$$LastAv=(1/16)* Count\_Val+(15/16)*LastAv\_Old \quad (2)$$

Variable LastAv stores the digitally smoothed representation of the patient's activity level. Variable LastAv_Old stores the LastAv value computed using Equation 2 during the previous cardiac cycle. At a heart rate of 72 bpm, the digital filter defined by Equation 2 has a time constant of approximately 13 seconds. During the first execution of the filter action 506, variable LastAv is effectively set to the value of Count-Val.

In a compute activity action 506, processor 460 uses the averaged sample to determine an activity value. In one example, LastAv is used to derive the patient's averaged activity level Activity by applying a recursive, low-pass digital filter to the value of LastAv according to Equation 3:

$$Activity=(1/65536)*LastAv+(65535/65536)*Act\_Avg\_Old \quad (3)$$

In the illustrative example, variable Act_Avg_Old represents the value of Act_Avg derived during the previous heartbeat cycle. At a pacing rate of 60 bpm, the time constant of the Activity digital filter is approximately 18 hours. Thus, variable Activity represents a running average of the patient's activity level, closely approximating the patient's rest activity level. During the first execution of the compute activity action 506 following initialization, the value Activity is effectively set equal to LastAv computed in filter action 504.

After determining sample, average, and activity values such as Count_Val, LastAv, and Activity, processor 460 fills an activity histogram in a fill activity histogram action 508. Generally, the fill activity histogram action 508 is a timed action so that histogram updating takes place at regular intervals. In one example, a health care provider can select the frequency of histogram updating. One suitable histogram update rate is approximately once every 26 seconds, less frequently than every heartbeat cycle to conserve space in the memory 494. The processor 460 uses the activity histogram to derive an activity threshold and, in turn, to determine whether the patient is sleeping or awake.

Figure 6A:
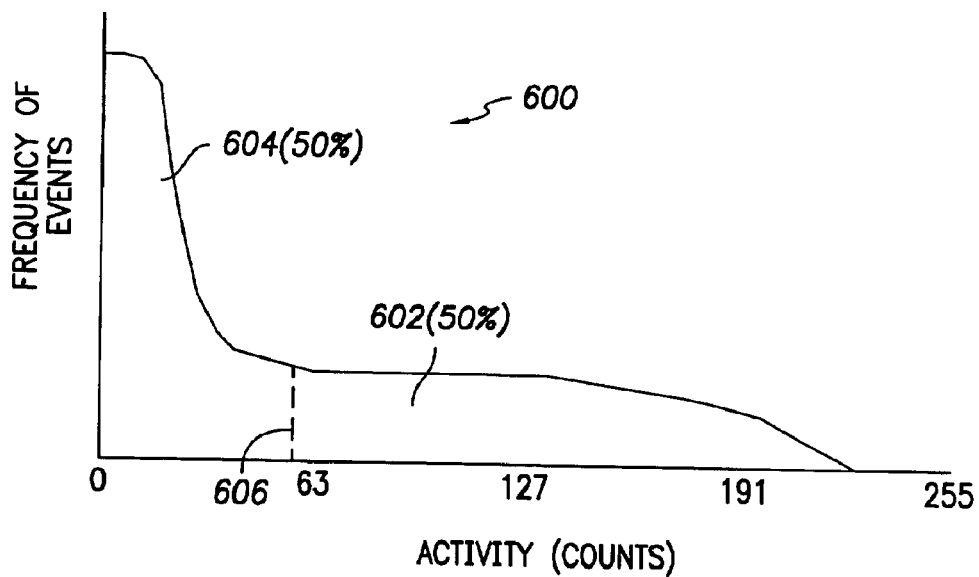
FIGS. 6A and 6B are graphs that respectively depict an example of an activity histogram that may be filled using the fill activity histogram action, and an example of an activity variance histogram that may be filled using the fill activity variance histogram action.

In fill activity histogram action 508, processor 460 increments the bin of the activity histogram designated by the Activity value. The activity histogram may be maintained in the memory 494. Referring to FIG. 6A, a graph depicts an example of an activity histogram 600 that may be filled using the fill activity histogram action 508. The activity histogram 600 is a distribution of the relative frequency of occurrence of activity values. In the illustrative histogram, the computed activity values can range from a minimum activity value of 0 to a maximum value of 255.

FIG. 6A shows an example of an activity histogram 600 containing data collected over a period of about one week for a typical patient. In one example, the activity histogram 600 is divided into 128 two-byte bins, each corresponding to an Activity value so that the activity histogram 600 occupies 256 bytes of memory 494.

Referring again to FIG. 5, an activity histogram fill complete logic action 510 tests to determine whether the histogram is completely filled. Histogram filling completion can be defined as the occurrence of an event such as a timing count, a completed number of samples, or external events including commands from an external programmer. The activity threshold is re-evaluated at preselected intervals, for example weekly. If the histogram fill is complete, processor 460 performs calculate and update activity threshold action 512.

In one example of a suitable calculate and update activity threshold action 512, processor 460 may estimate a Sleep_Events value that is indicative of the number of activity measurements stored in the activity histogram that were derived while the patient was sleeping. Processor 460 determines Sleep_Events according to equation 4:

$$Sleep\_Events=(Sleep\_Hrs/24)*Total\_Events \quad (4)$$

Variable Sleep_Hrs designates the number of hours the patient typically spends sleeping each day, according to programming in initialization action 500. Variable Total_Events designates the total number of activity measurements stored in the activity histogram at the time of the sleep event. A weekly histogram contains about 23,296 total events.

In one example of a technique to calculate activity threshold, processor 460 uses the Sleep_Events value to determine the activity threshold Act_Thresh. Processor 460 adds contents of all activity histogram bins starting with the lowest bin and proceeding through successively higher bins until the number of measurements corresponding to the value of Sleep-Events are counted. The final added bin is deemed to be the highest bin containing activity measurements that were derived during patient sleep. Variable Act_Thresh is set to the activity value associated with the highest added bin. In the example shown in FIG. 6A, activity threshold 606 divides the activity histogram 600 into two regions including a nonactive region 604 for lower activity samples and an active region 606 for high activity samples. In the illustrative example, the nonactive region 604 and the active region 606 each contain about half the sample values.

After determining activity variance threshold, processor 460 clears the activity histogram in clear activity histogram action 514 to prepare for collection of new data over the next update period.

After clearing the activity histogram or in cases the activity histogram is not filled, processor 460 computes an activity difference value in compute absolute difference of adjacent activity action 516. The processor 460 determines the absolute difference of adjacent Activity values. A sequence of activity sample data measurements and calculated Activity values are acquired, typically with a predetermined constant time interval separating the samples. In various embodiments, the precision of the time intervals may vary. The processor 460 determines the absolute value difference between two adjacent Activity values, for example according to equation 5:

$$Diff=ABS(Last\_Av\_Last\_Av\_Old) \quad (5)$$

In a lowpass filter absolute difference action 518, processor 460 computes the difference variable Diff as the absolute value of the difference between the LastAv current value of and LastAv computed at the last histogram update. In some embodiments, the processor 460 digitally smoothes the difference Diff using a recursive, low pass filter, for example according to Equation 6:

$$Act\_var=(1/32)*Diff+(31/32)*Act\_Var\_Old \quad (6)$$

Variable Act_Var stores the current smoothed difference. Variable Act_Var_Old stores the prior smoothed difference.

Variable Act_Var is set to the value Diff in the first update after initialization.

Referring to FIG. 6, the flowchart continues with a calculate activity variance action 520. Processor 460 uses the filtered activity variance to determine an activity variance value. In one example, Act_var is used to derive the patient's averaged activity variance level Activity_Variance by applying a recursive, low-pass digital filter to the value of Act_var according to Equation 7:

$$\text{Activity\_Variance} = (1/65536)*\text{Act\_var} + (65535/65536)*\text{Act\_var\_Old} \quad (7)$$

In the illustrative example, variable Act_var_Old represents the value of Act_var derived during the previous heartbeat cycle. At a pacing rate of 60 bpm, the time constant of the Activity_Variance digital filter is approximately 18 hours. Thus, variable Activity_Variance represents a running average of the patient's activity level, closely approximating the patient's rest activity variance level. During the first execution of the calculate activity variance action 520 following initialization, the value Activity_Variance is effectively set equal to Act_var computed in lowpass filter absolute difference action 518.

After determining the activity variance value, processor 460 fills an activity histogram in a fill activity variance histogram action 522. Generally, the fill activity variance histogram action 522 is a timed action so that histogram updating takes place at regular intervals. A suitable histogram update rate is approximately once every 26 seconds, less frequently than every heartbeat cycle to conserve space in the memory 494. The processor 460 uses the activity variance histogram to derive an activity threshold and, in turn, to determine whether the patient is sleeping or awake.

Figure 6B:
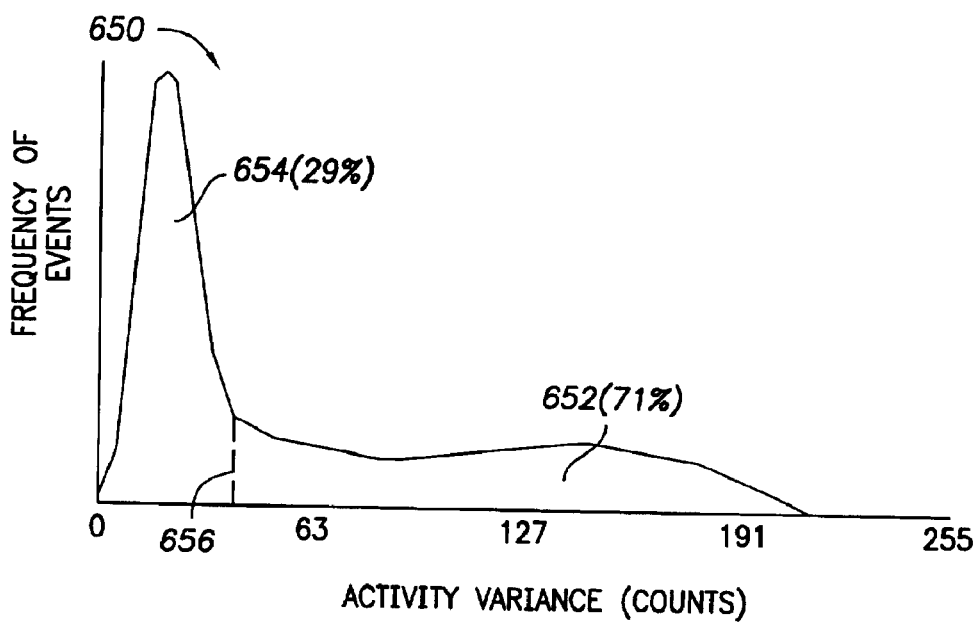

In fill activity variance histogram action 522, processor 460 increments the bin of the activity variance histogram designated by the Activity-variance value. The activity variance histogram may be maintained in the memory 494. Referring to FIG. 6B, a graph depicts an example of an activity variance histogram 650 that may be filled using the fill activity variance histogram action 522. The activity variance histogram 650 is a distribution of the relative frequency of occurrence of activity variance values. In the illustrative histogram, the computed activity values can range from a minimum activity variance value of 0 to a maximum value of 255.

FIG. 6B shows an example of an activity variance histogram 650 containing data collected over a period of about one week for a typical patient. In one example, the activity variance histogram 650 is divided into 128 two-byte bins, each corresponding to an Activity_Variance value so that the activity variance histogram 650 occupies 256 bytes of memory 494.

Referring again to FIG. 6, an activity variance histogram fill complete logic action 524 tests to determine whether the histogram is completely filled. Histogram filling completion can be defined as the occurrence of an event such as a timing count, a completed number of samples, or external events including commands from an external programmer. The activity variance threshold is re-evaluated at preselected intervals, for example weekly. If the histogram fill is complete, processor 460 performs calculate and update activity variance threshold action 526.

In one example of a suitable calculate and update activity variance threshold action 526, processor 460 may estimate a Sleep_Events value that is indicative of the number of activity variance measurements stored in the activity variance histogram that were derived while the patient was sleeping. Processor 460 can determine Sleep_Events according to equation 4.

Variable Sleep_Hrs designates the number of hours the patient typically spends sleeping each day, according to programming in initialization action 500. Variable Total_Events designates the total number of activity variance measurements stored in the activity variance histogram at the time of the sleep event. A weekly histogram contains about 23,296 total events.

In one example of a technique to calculate activity threshold, processor 460 uses the Sleep_Events value to determine the activity variance threshold Act_Var_Thresh. Processor 460 adds contents of all activity variance histogram bins starting with the lowest bin and proceeding through successively higher bins until the number of measurements corresponding to the value of Sleep-Events are counted. The final added bin is deemed to be the highest bin containing activity variance measurements that were derived during patient sleep. Variable Act_Var_Thresh is set to the activity variance value associated with the highest added bin. In the example shown in FIG. 6B, activity variance threshold 656 divides the activity variance histogram 650 into two regions including a nonactive region 654 for lower activity variance samples and an active region 656 for high activity variance samples. In the illustrative example, the nonactive region 654 and the active region 656 each contain about half the sample values.

The activity variance histogram 650 typically is characterized by a bimodal distribution with a higher mode 652 corresponding to activity variance measurements derived during the day while the patient is awake but relatively inactive. A lower mode 654 is a dominant mode and corresponds to activity variance measurements derived during sleep.

A bin 656 of activity variance histogram 650 is designated by the variable Act_Var_Thresh and corresponds to an activity variance measurement of about 2.5 counts. The bin 656 is estimated to be the highest bin of activity variance histogram 650 that contains activity variance measurements derived for a sleeping patient.

After determining activity variance threshold, processor 460 clears the activity variance histogram in clear activity variance histogram action 528 to prepare for collection of new data over the next update period.

After clearing the activity histogram or in cases the activity histogram is not filled, processor 460 determines whether the patient is in a resting or sleeping condition in detect rest or sleep logic action 530.

Figure 7:
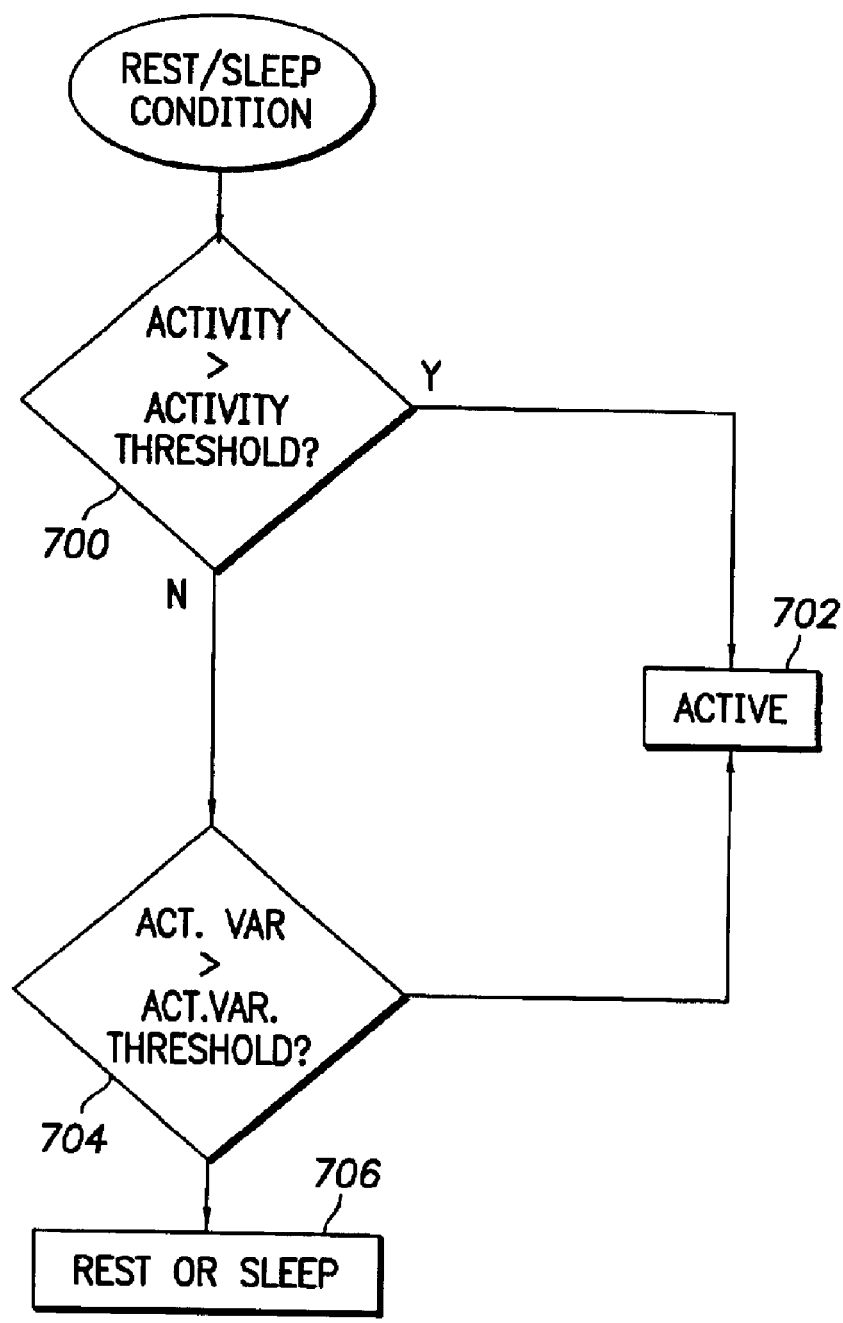
FIG. 7 is a schematic flowchart depicting an example of a suitable detect rest or sleep logic action.

Referring to FIG. 7, a schematic flow chart depicts an example of a suitable detect rest or sleep logic action 530. In a test activity logic block 700, processor 460 tests the current activity value to determine whether the current activity is greater than the activity threshold. If the current activity is greater than the activity threshold, the patient is in the active state 702. Otherwise processor 460 tests the activity variance 704 to determine whether the activity variance is greater than the activity variance threshold. If activity variance exceeds the threshold, the patient is in the active state 702. Otherwise, the patient is in a rest or sleep state 706.

Referring again to FIG. 5B, if the detect rest or sleep logic action 530 determines that the state is the active state 702, then control loops back to read sensor and clear action 502 to continue activity sampling. In the rest or sleep state 706, processor 460 delivers sleep apnea preventive therapy 532. Following delivery of the preventive therapy 532 control loops back to read sensor and clear action 502 to continue activity sampling.

When the patient is sleeping and sleep apnea preventive pacing is indicated, the system may deliver a sleep apnea preventive therapy. Most generally, sleep apnea preventive pacing is cardiac pacing at a rate higher than the sleeping rate, Sleep_Rate. Various techniques can be used that prevent sleep apnea based on elevation of the cardiac rate during sleep.

In one example, processor 460 continues pacing with the pacing rate set to the Sleep_Rate value. Processor 460 can set the pacing rate to the lower Sleep_Rate level for the current heartbeat cycle by instructing the timing control circuitry 479 to lengthen the escape interval.

If another example, activity and activity variance can be monitored to determine patient state among multiple possible states including active, at rest but awake, asleep, or other levels of activity. Cardiac rate is then set according to the particular current patient state.

In another example, the processor 460 does not simply switch the base pacing rate between a sleeping rate and a resting rate but rather can use activity variance measurements to set the pacing rate to rates between a sleeping rate and a resting rate. More specifically, although the base pacing rate is bounded on the low end by a preprogrammed sleeping rate, the base pacing rate has no predetermined upper limit or resting rate. The second example does not use an activity variance histogram but rather employs a preprogrammed base rate slope applied to the activity variance measurements to determine the amount to increase the base pacing rate above the sleeping rate.

A system that generates neuromuscular stimulation synchronized with respiration for prevention and treatment of respiratory disorders such as sleep apnea typically includes a respiration sensor, a neurostimulator, and a signal processing capability responsive to signals from the respiration sensor to generate stimulation signals of suitable amplitude, location, and timing. One example of a suitable respiration sensor uses impedance sensing by the ventricular sensing circuit 484 and/or the atrial sensing circuit 482 to periodically measure transthoracic impedance between a lead implanted in the patient's heart and an indifferent electrode, such as the device housing 440. Transthoracic impedance is proportional to chest volume and indicates the degree and rate of patient chest expansion and contraction.

Figure 8:
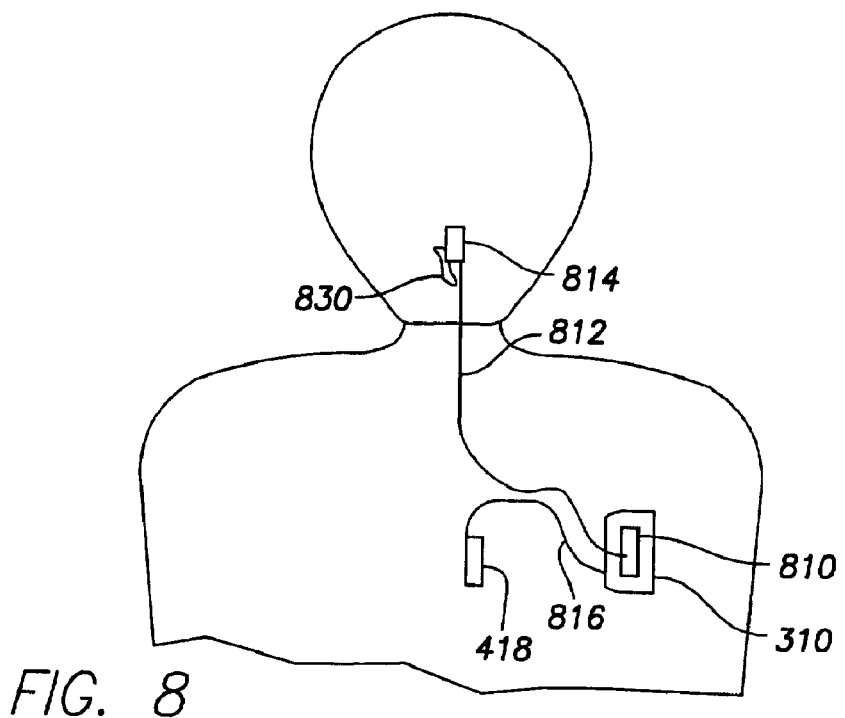
FIG. 8 is a frontal sectional view of a patient showing implantable components of a stimulation device capable of detecting and treating sleep apnea.

Referring to FIG. 8, a schematic block diagram illustrates an example of a stimulation device 310 that includes sensors and stimulators for detecting and treating sleep apnea. An implantable neurostimulator 810 is capable of generating one or more neurostimulation pulses through a neurostimulation lead 812 that passes to an electrode system 814 positionable in the vicinity of muscle or nerve such as hypoglossal nerve 830. Stimulation of the hypoglossal nerve 830 stimulates the genioglossus muscle of the upper airway. Electrode system 814 is positionable in the vicinity of any suitable nerve or muscle to perform a desired treatment.

The implantable neurostimulator 810 is connected to the physiological sensor 418, here a respiration sensor, to receive a respiration waveform via a sensor lead 816. The respiration sensor senses a respiration signal, typically performs some signal conditioning or filtering, and transfers the respiration waveform to the implantable neurostimulator 810 via the sensor lead 816. The implantable neurostimulator 810 may generate timing of neurostimulation pulses to synchronize with the patient's respiratory cycle.

Figure 9:
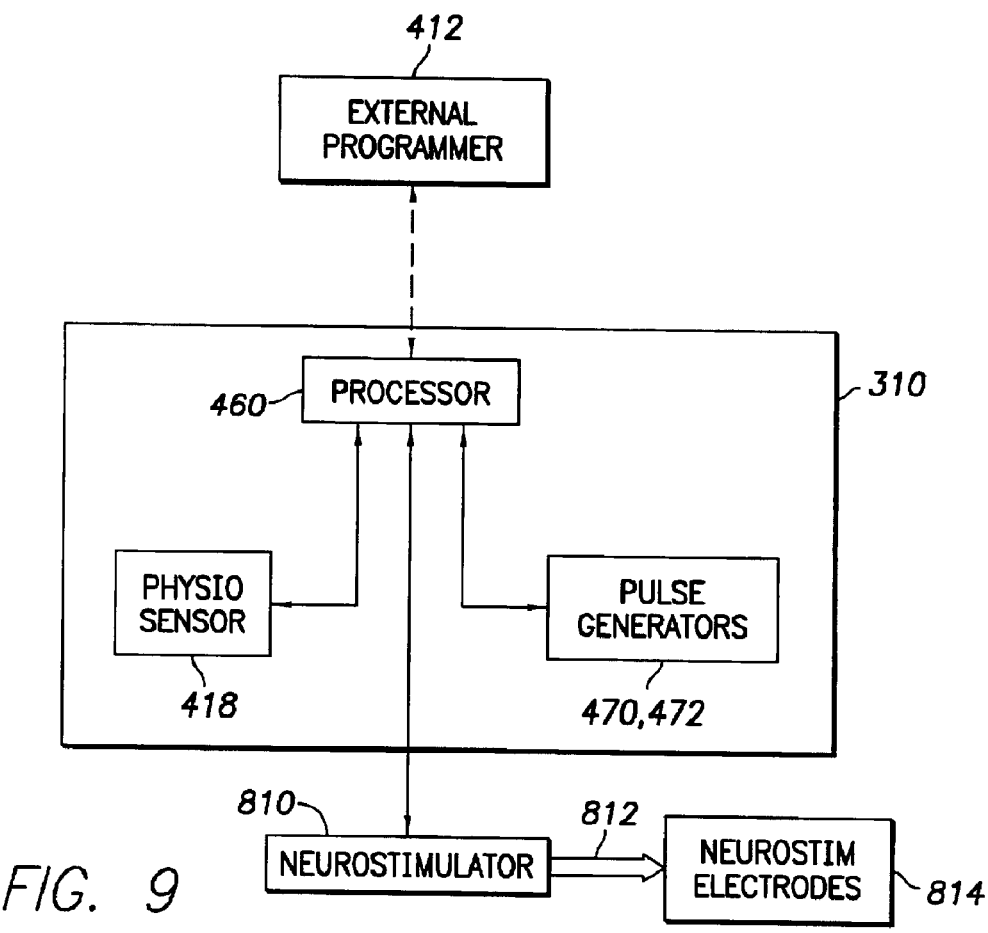
FIG. 9 is a schematic block diagram showing an example of the stimulation device shown in FIG. 8 including device programming components.

Referring to FIG. 9, the neurostimulator system includes an external programming device 412 including programming software and communication capabilities for communicating with implantable neurostimulator 810. The external programmer 412 is normally used to program the stimulation device 310 and implantable neurostimulator 810 with various parameters that adapt operations to the needs of a particular patient. For example, the external programmer 412 can be used to activate or deactivate neurostimulation, adjust neurostimulation amplitude within predetermined limits, pulse frequency, pulse pattern, and pulse delay time.

The neurostimulation electrode system 814 may be any conventional electrode or electrode system that is suitable for stimulation of muscles or nerves for respiratory disorder treatments. Various muscles and/or nerves may be stimulated, depending on the particular application and condition. For example, the neurostimulation electrode system 814 may be placed in the vicinity of a respiratory motor nerve such as the hypoglossal nerve, and connected to the implantable neurostimulator 810 by the neurostimulation lead 812. The implantable neurostimulator 810 is activated to deliver a controlled sequence of neurostimulation pulses to the muscle or nerve. For example, one or more neurostimulation pulses can be delivered to the neurostimulation electrode system 814 and transferred to the nerve to cause opening of the airway during respiration.

Processor 460 can be configured to coordinate generation of neurostimulation pulses in synchrony with signals sensed by a physiological sensor 418, specifically a respiration signal sensor. For example, the processor 460 analyzes respiratory signal data and may, as one level of apnea treatment, generate neurostimulation pulses timed according to respiratory events.

Figure 10:
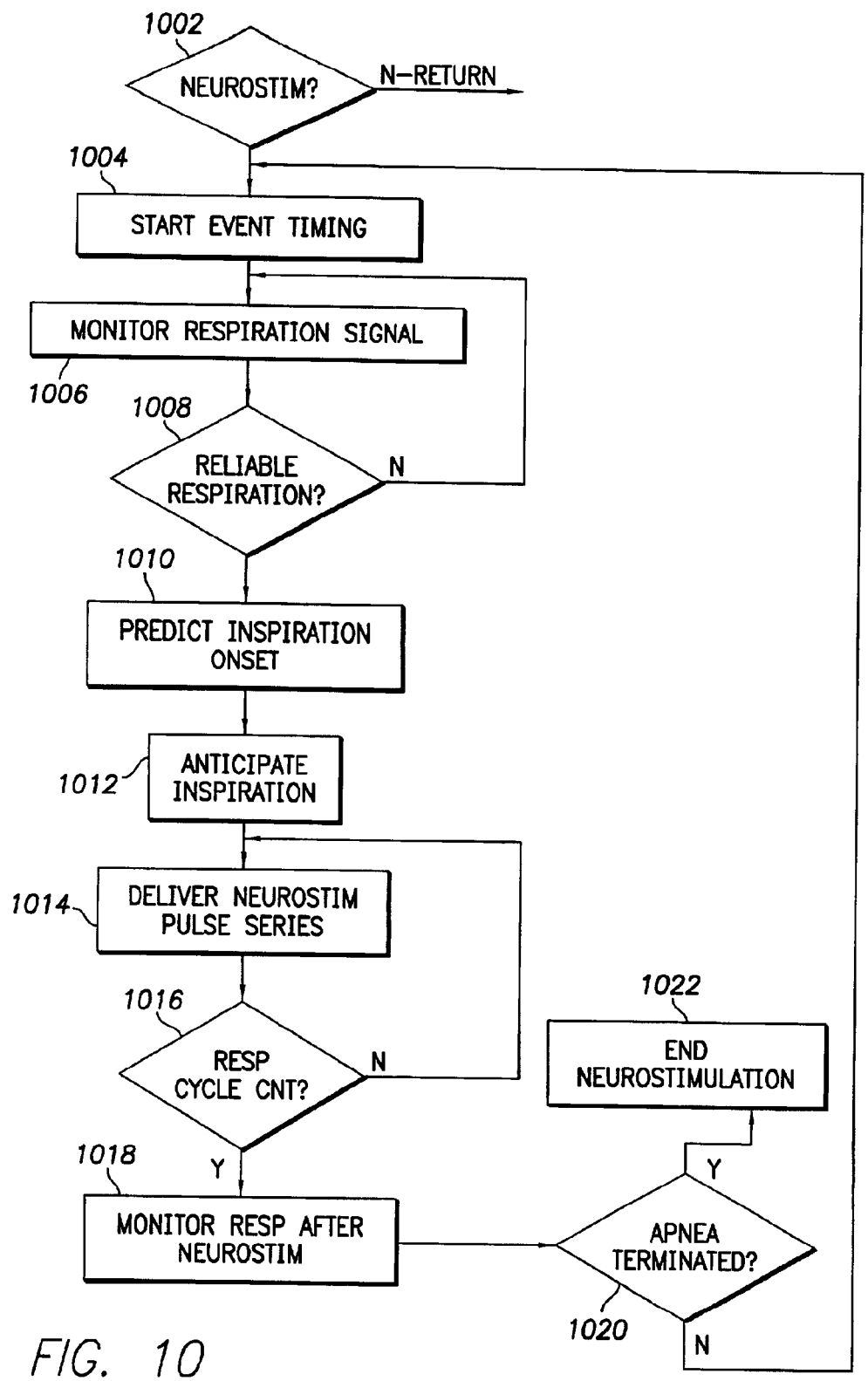
FIG. 10 is a schematic flow chart that illustrates actions of the stimulation device when a pacing therapy fails to terminate sleep apnea, and a more extreme level of intervention is appropriate.
Figure 11:
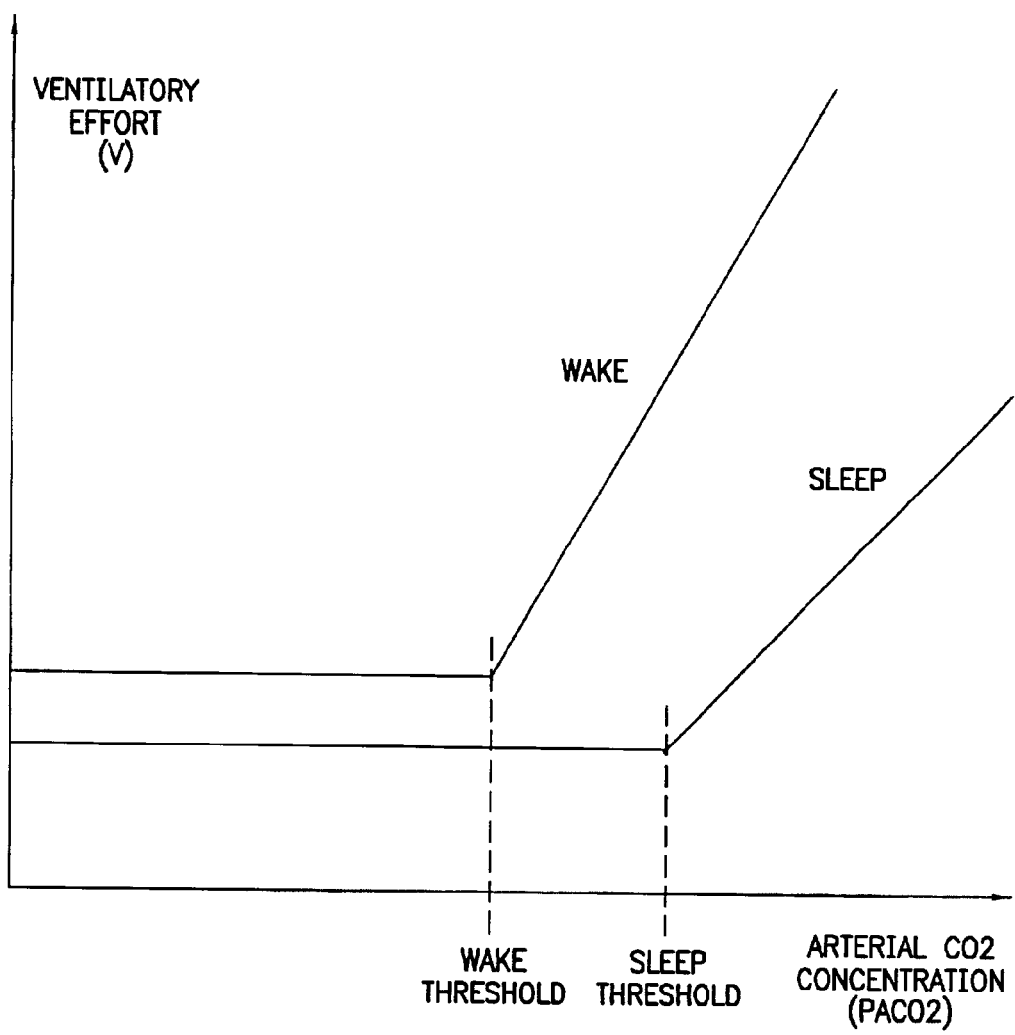
FIG. 11 is a graph that illustrates the mechanism of sleep apnea by correlating ventilatory effort to arterial partial pressure of carbon dioxide ($PaCO_2$).

Referring to FIG. 10 a schematic flow chart illustrates actions of the stimulation device 310 when a pacing therapy fails to terminate sleep apnea, and a more extreme level of intervention is appropriate. Processor 460 determines 1002 that sleep apnea is to be terminated by delivery of neurostimulation, and begins a sequence of timed actions 1004. In one example, processor 460 monitors the respiration signal 1006 to determine when the patient begins inspiration in each cycle of a series of respiratory cycles. Processor 460 tracks the timing of inspiration onset to predict the time of inspiration onset in subsequent cycles. When monitoring indicates a reliable respiratory timing 1008, processor 460 predicts the next inspiration onset time 1010 and anticipates the predicted inspiration onset time by a predetermined onset interval 1012, for example 200 ms.

Processor 460 generates a series of neurostimulation pulses within a single respiratory cycle 1014 beginning the onset interval time prior to the predicted inspiration onset. The neurostimulation pulses are delivered at a suitable frequency, for example one range of frequencies may be from 1–60 Hz, although other frequencies are possible. Anticipatory neurostimulation allows recruitment of muscle fibers to assist ventilation. The number of pulses and the interval between pulses for the respiratory cycle is preset for the particular patient. The interval between pulses may be fixed or changing, for example in either an increasing or decreasing ramp. Although respiratory cycle timing has some nonuniformity, the system operates reliably with typical timing variations. The stimulation device 310 delivers the neurostimulation pulses for a preset number of respiration cycles 1016. Neurostimulation may be selected for consecutive cycles or with a predetermined number of respiration cycles between a respiratory cycle with neurostimulation.

Processor 460 controls neurostimulation on the basis of the detected respiration signal. Processor 460, on detection of signal artifacts or nonperiodic respiration, may suspend neurostimulation. Nonperiodic respiration may be indicated by one or more respiratory cycle intervals that fall outside preset limits.

Monitoring continues 1018 during or following the neurostimulation cycles to determine whether neurostimulation has terminated a sleep apnea episode. If sleep apnea is terminated 1020, neurostimulation is inactivated 1022.

In some embodiments, the stimulation device 310 may utilize the pulse generator 338 as a neurostimulator, so that a separate neurostimulator is not required. In these embodiments, a lead such as a left ventricular epicardial lead 324 or a coronary sinus lead 324 may be implanted in the vicinity of the phrenic nerve and electrical pulses generated on the lead so that the phrenic nerve is stimulated, resulting in activation of muscles that assist respiration.

While the invention has been described with reference to various embodiments, it will be understood that these embodiments are illustrative and that the scope of the invention is not limited to them. Many variations, modifications, additions and improvements of the embodiments described are possible. For example, those of ordinary skill in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. An implantable cardiac stimulation device for implantation in a body comprising:
    a metabolic demand sensor that is capable of sensing a parameter indicative of the body's metabolic demand;
    an activity sensor that is capable of sensing a parameter indicative of physical activity of the body;
    circuitry connected to the respective sensors and that is operative to process signals from the respective sensors to detect a sleep apnea condition;
    one or more pulse generators that are capable of generating cardiac pacing pulses, wherein the circuitry is responsive to the detected sleep apnea condition to control the one or more pulse generators to generate cardiac pulses with a timing that tends to terminate the detected sleep apnea condition; and
    a neurostimulator coupled to respiratory muscles of the body's upper airways or diaphragm, the neurostimulator being adapted to generate neurostimulation pulses for terminating the detected sleep apnea condition if the generated cardiac pacing pulses fail to terminate the detected sleep apnea condition.

2. An implantable cardiac stimulation device according to claim 1 wherein the circuitry comprises a controller coupled to the one or more pulse generators and to the metabolic demand and activity sensors, the controller including an executable control logic that detects a sleep condition and controls the one or more pulse generators to generate pacing pulses with a timing based on a comparative analysis of the metabolic demand-indicative parameter and the physical activity-indicative parameter performed by the controller that is capable of terminating the detected sleep apnea condition.

3. An implantable cardiac stimulation device according to claim 1 wherein the circuitry comprises a controller coupled to the one or more pulse generators and to the metabolic demand and activity sensors, the controller including an executable control logic that detects a sleep condition upon a determination that the metabolic demand-indicative parameter end the physical activity-indicative parameter are at low resting levels and detects the detected sleep apnea condition upon a determination that the metabolic demand-indicative parameter diverges to a lower level relative to the physical activity-indicative parameter.

4. An implantable cardiac stimulation device according to claim 1 wherein the circuitry comprises a controller coupled to the one or more pulse generators and to the metabolic demand and activity sensors, the controller including an executable control logic that detects a sleep apnea condition and controls the one or more pulse generators with a timing based on one or more of the metabolic demand-indicative parameter and the physical activity-indicative parameter that is capable of treating the detected sleep apnea condition.

5. An implantable cardiac stimulation device according to claim 1 wherein the circuitry comprises a controller coupled to the one or more pulse generators and to the metabolic demand and activity sensors, the controller including an executable control logic that distinguishes between a sleeping condition and a waking condition of a patient, and controls the one or more pulse generators to generate pacing pulses with a timing based on a comparative analysis of the metabolic demand-indicative parameter and the physical activity-indicative parameter performed by the controller that is capable of terminating the detected sleep apnea condition.

6. An implantable cardiac stimulation device according to claim 1 wherein the circuitry comprises a controller coupled to the one or more pulse generators and to the metabolic demand and activity sensors, the controller including an executable control logic that controls the one or more pulse generators to pace at a rate selected from among at least a sleeping rate, a resting rate, and an exercising rate, the executable control logic being capable of distinguishing between a sleeping condition and a waking condition based on a comparative analysis of the metabolic demand-indicative parameter and the physical activity-indicative parameter performed by the controller, and controlling the one or more pulse generators to pace at a rate greater than the resting rate in response to detection of a sleeping condition.

7. An implantable cardiac stimulation device according to claim 1 further comprising:
    a transthoracic impedance sensor that is capable of sensing a respiration parameter and functioning as the metabolic demand sensor; and
    an accelerometer that is capable of sensing a physical activity parameter and functioning as the activity sensor.

8. An implantable cardiac stimulation device according to claim 1 further comprising:
    a physiological sensor that measures blood oxygen concentration and wherein the circuitry activates sleep apnea preventive pacing when blood oxygen concentration is depressed during sleep.

9. An implantable cardiac stimulation device according to claim 1 further comprising:
    a physiological sensor that measures blood carbon dioxide concentration and wherein the circuitry activates sleep apnea preventive pacing when blood carbon dioxide concentration is elevated during sleep.

10. An implantable cardiac stimulation device for implantation in a body comprising:
    a metabolic demand sensor that is capable of sensing a parameter indicative of the body's metabolic demand;
    an activity sensor that is capable of sensing a parameter indicative of physical activity of the body;
    one or more pulse generators that are capable of generating cardiac pacing pulses with a timing based on the metabolic demand-indicative parameter and the physical activity-indicative parameter, the timed cardiac pacing pulses for treating a first level of sleep apnea; and a neurostimulator that is capable of coupling to respiratory muscles of the body's upper airways or diaphragm and generating neurostimulation pulses treating a second level of sleep apnea if the generation of the cardiac pacing pulses fails to terminate the first level of sleep apnea.

11. An implantable cardiac stimulation device according to claim 10 further comprising:

a controller coupled to the one or more pulse generators, the metabolic demand and activity sensors, and the neurostimulator, the controller including an executable control logic that detects a sleep condition and a sleep apnea condition based on the metabolic demand-indicative parameter and the physical activity-indicative parameter.

12. An implantable cardiac stimulation device according to claim 10 further comprising:

a controller coupled to the one or more pulse generators, the metabolic demand and activity sensors, and the neurostimulator, the controller including an executable control logic that distinguishes between a sleeping condition, a waking condition, and a sleep apnea condition of a patient, and controls the one or more pulse generators to generate pacing pulses with a timing based on a comparative analysis of the metabolic demand-indicative parameter and the physical activity-indicative parameter performed by the controller that is capable of treating the sleep apnea condition.

13. An implantable cardiac stimulation device according to claim 10 further comprising:

a controller coupled to the one or more pulse generators, the metabolic demand and activity sensors, and the neurostimulator, the controller including an executable control logic that controls the one or more pulse generators to pace at a rate selected from among at least a sleeping rate, a resting rate, and an exercising rate, the executable control logic being capable of distinguishing between a sleeping condition, a waking condition, and a sleep apnea condition based on comparative analysis of the metabolic demand-indicative parameter and the physical activity-indicative parameter performed by the controller, and controlling the one or more pulse generators to pace at a rate greater than the resting rate in response to detection of a sleeping condition and a further increased rate in response to detection of a sleep apnea condition.

14. An implantable cardiac stimulation device according to claim 10 further comprising:

a transthoracic impedance sensor that capable of sensing a respiration parameter and functioning as the metabolic demand sensor; and an accelerometer of piezoelectric crystal sensor that is capable of sensing a physical activity parameter and functioning as the activity sensor.

15. A method of operating an implantable cardiac stimulation device comprising:

generating cardiac pacing pulses at a predetermined rate;

sensing a parameter indicative of a body's metabolic demand;

sensing a parameter indicative of physical activity of the body;

analyzing a plurality of sensed metabolic demand parameters and a plurality of sensed physical activity parameters to determine if a sleep apnea condition exists; and controlling the cardiac pacing pulses according to a sleep apnea prevention mode to terminate the detected sleep apnea condition; and generating neurostimulation pulses for application to the body's upper airways or diaphragm to terminate the sleep apnea condition if the cardiac pacing pulses fail to terminate the sleep apnea condition.

16. A method according to claim 15 further comprising:

analyzing a sequence of sensed metabolic demand parameters in comparison with a sequence of sensed physical activity parameters to determine a sleep condition.

17. A method according to claim 15 further comprising:

analyzing a sequence of sensed metabolic demand parameters in comparison with a sequence of sensed physical activity parameters to determine the sleep apnea condition.

18. A method according to claim 15 further comprising:

detecting a sleep condition upon a determination that the metabolic demand-indicative parameter and the physical activity-indicative parameter are at low resting levels.

19. A method according to claim 15 further comprising:

detecting the sleep apnea condition upon a determination that the metabolic demand-indicative parameter diverges to a lower level relative to the physical activity-indicative parameter.

20. An implantable cardiac stimulation device comprising:

means for sensing a parameter indicative of the body's metabolic demand;

means for sensing a parameter indicative of physical activity of the body;

means for generating cardiac pacing pulses; and means for detecting a sleep apnea condition based on the respective means for sensing; and means for controlling the means for generating according to a sleep apnea prevention mode when the sleep apnea condition is detected; and means for generating neurostimulation pulse for application to the body's upper airways or diaphragm to terminate the sleep apnea condition if the generation of cardiac pulses fails to terminate the sleep apnea condition.

21. An implantable cardiac stimulation device according to claim 20 further comprising:

means for detecting a sleep condition upon a determination that the metabolic demand-indicative parameter and the physical activity-indicative parameter are at low resting levels.

22. An implantable cardiac stimulation device according to claim 20 further comprising:

means for detecting the sleep apnea condition upon a determination that the metabolic demand-indicative parameter diverges to a lower level relative to the physical activity-indicative parameter.

* * * * *